US007795310B2

(12) United States Patent
Lee et al.

(10) Patent No.: US 7,795,310 B2
(45) Date of Patent: Sep. 14, 2010

(54) METHODS AND REAGENTS FOR THE TREATMENT OF METABOLIC DISORDERS

(75) Inventors: Margaret S. Lee, Middleton, MA (US); Grant R. Zimmermann, Somerville, MA (US); Alyce L. Finelli, Framingham, MA (US); Daniel Grau, Cambridge, MA (US); Curtis Keith, Boston, MA (US); M. James Nichols, Boston, MA (US)

(73) Assignee: CombinatoRx, Inc., Cambridge, MA (US)

( * ) Notice: Subject to any disclaimer, the term of this patent is extended or adjusted under 35 U.S.C. 154(b) by 0 days.

(21) Appl. No.: 11/171,566

(22) Filed: Jun. 30, 2005

(65) Prior Publication Data
US 2006/0069161 A1 Mar. 30, 2006

Related U.S. Application Data

(60) Provisional application No. 60/584,380, filed on Jun. 30, 2004, provisional application No. 60/649,329, filed on Feb. 2, 2005.

(51) Int. Cl.
*A61K 31/19* (2006.01)
(52) U.S. Cl. ............ 514/568; 514/571; 514/866
(58) Field of Classification Search .......... 514/568, 514/571, 866
See application file for complete search history.

(56) References Cited

U.S. PATENT DOCUMENTS

| 6,194,454 B1 * | 2/2001 | Dow ................... 514/522 |
| 6,500,823 B1 * | 12/2002 | Literati Nagy et al. ... 514/231.5 |
| 6,576,256 B2 | 6/2003 | Liang et al. |
| 6,593,347 B2 * | 7/2003 | Bandarage et al. .......... 514/327 |
| 2002/0016293 A1 * | 2/2002 | Ratain et al. ............... 514/9 |

FOREIGN PATENT DOCUMENTS

| WO | WO 03/059294 | 7/2003 |
| WO | WO 03/082283 | 10/2003 |
| WO | WO 2004/052362 | 6/2004 |
| WO | WO 2005/025673 | 3/2005 |

OTHER PUBLICATIONS

Tenenbaum et al., "Peroxisome Proliferator-Activated Receptor Ligand Bezafibrate for Prevention of Type 2 Diabetes Mellitus in Patients With Coronary Artery Disease", Circulation, 2004, pp. 2197-2202.*
Shen et al., "Effect of gemfibrozil treatment in sulfonylurea-treated patients with noninsulin-dependent diabetes mellitus", The Journal of Clinical Endocrinology & Metabolism, vol. 73, pp. 503-510, 1991(see enclosed abstract).*
International Search Report from PCT/US2005/023030, mailed Dec. 1, 2005.
Lin et al., "Effect of Experimental Diabetes on Elimination Kinetics of Diflunisal in Rats," Drug Metab. Dispos. 17:147-152 (1989). Abstract only.
Neogi et al., "Synthesis and Structure-Activity Relationship Studies of Cinnamic Acid-Based Novel Thiazolidinedione Antihyperglycemic Agents," Bioorg. Med. Chem. 11:4059-4067 (2003).
Vessby et al., "Effects of Bezafibrate on the Serum Lipoprotein Lipid and Apolipoprotein Composition, Lipoprotein Triglyceride Removal Capacity and the Fatty Acid Composition of the Plasma Lipid Esters," Atherosclerosis 37:257-269 (1980). Abstract only.
Windholz et al., eds., "Abstract No. 4866," *The Merck Index*. 10th ed., p. 723-724, Merck and Company, Inc.: Rahway, NJ (1983).
Sone et al., "Ibuprofen-Related Hypoglycemia in a Patient Receiving Sufonylurea" *Annals of Internal Medicine* 134:344, 2001.
Yuan et al., "Reversal of Obesity- and Diet-Induced Insulin Resistance with Salicylates or Targeted Disruption of *Ikkβ*" Science 293:1673-1677, 2001.
Search Report from European Application No. 05768186 mailed on Jun. 2, 2008.
Chen et al., "The Pharmacological Interactions of Antihyperglycemic Agents (1)", *Journal of Chinese Physician* 29:47, 2001.
Communication from the State Intellectual Property Office of the People's Republic of China for Application No. 2005800289684 with English translation (issued Jul. 17, 2009), (pp. 1-16).
Yang et al., "The Comparison of Treatment of Type 2 Diabetes Mellitus Complicated with Hyperlipemia with Bezafibrate and Pravastatin Sodium", *Shanghai Medical Journal* 21:478-480, 1998.

* cited by examiner

*Primary Examiner*—Kevin Weddington
(74) *Attorney, Agent, or Firm*—Clark & Elbing LLP

(57) ABSTRACT

The invention features compositions, methods, and kits for the treatment of metabolic disorders such as diabetes and obesity.

6 Claims, 3 Drawing Sheets

METHODS AND REAGENTS FOR THE TREATMENT OF METABOLIC DISORDERS

CROSS-REFERENCE TO RELATED APPLICATIONS

This application claims benefit from U.S. Ser. No. 60/584,380, filed Jun. 30, 2004, and U.S. Ser. No. 60/649,329, filed Feb. 2, 2005, each of which is hereby incorporated by reference.

BACKGROUND OF THE INVENTION

The invention relates to the treatment, prevention, and reduction of metabolic disorders, such as diabetes and obesity.

As the levels of blood glucose rise postprandially, insulin is secreted and stimulates cells of the peripheral tissues (skeletal muscles and fat) to actively take up glucose from the blood as a source of energy. Loss of glucose homeostasis as a result of faulty insulin secretion or action typically results in metabolic disorders such as diabetes, which may be co-triggered or further exacerbated by obesity. Because these conditions are often fatal, strategies to restore adequate glucose clearance from the bloodstream are required.

Although diabetes may arise secondary to any condition that causes extensive damage to the pancreas (e.g., pancreatitis, tumors, administration of certain drugs such as corticosteroids or pentamidine, iron overload (e.g., hemochromatosis), acquired or genetic endocrinopathies, and surgical excision), the most common forms of diabetes typically arise from primary disorders of the insulin signaling system. There are two major types of diabetes, namely type 1 diabetes (also known as insulin dependent diabetes (IDDM)) and type 2 diabetes (also known as insulin independent or non-insulin dependent diabetes (NIDDM)), which share common long-term complications in spite of their different pathogenic mechanisms.

Type 1 diabetes, which accounts for approximately 10% of all cases of primary diabetes, is an organ-specific autoimmune disease characterized by the extensive destruction of the insulin-producing beta cells of the pancreas. The consequent reduction in insulin production inevitably leads to the deregulation of glucose metabolism. While the administration of insulin provides significant benefits to patients suffering from this condition, the short serum half-life of insulin is a major impediment to the maintenance of normoglycemia. An alternative treatment is islet transplantation, but this strategy has been associated with limited success.

Type 2 diabetes, which affects a larger proportion of the population, is characterized by a deregulation in the secretion of insulin and/or a decreased response of peripheral tissues to insulin, i.e., insulin resistance. While the pathogenesis of type 2 diabetes remains unclear, epidemiologic studies suggest that this form of diabetes results from a collection of multiple genetic defects or polymorphisms, each contributing its own predisposing risks and modified by environmental factors, including excess weight, diet, inactivity, drugs, and excess alcohol consumption. Although various therapeutic treatments are available for the management of type 2 diabetes, they are associated with various debilitating side effects. Accordingly, patients diagnosed with or at risk of having type 2 diabetes are often advised to adopt a healthier lifestyle, including loss of weight, change in diet, exercise, and moderate alcohol intake. Such lifestyle changes, however, are not sufficient to reverse the vascular and organ damages caused by diabetes.

Given that the strategies currently available for the management of diabetes are suboptimal, there is a compelling need for treatments that are more effective and are not associated with such debilitating side-effects.

SUMMARY OF THE INVENTION

The present invention features compositions, methods, and kits for treating, preventing, and reducing metabolic disorders. This invention is particularly useful for treating patients having or at risk of having any condition that is characterized by a state of hyperglycemia, which may be caused, for example, by an alteration in the insulin signaling pathway (e.g., a reduction in insulin production, resistance to insulin, or both). Exemplary disorders amenable to treatment according to this invention are obesity, diabetes (e.g., type 1 diabetes, type 2 diabetes, maturity-onset diabetes of the young (MODY), and gestational diabetes), satiety, endocrine deficiencies of aging, and any of their associated complications (e.g., Syndrome X, diabetic retinopathy, diabetic nephropathy, diabetic neuropathy, peripheral vascular disease, hyperlipidemia, hypertension, atherosclerosis, and coronary heart disease).

In a first aspect, the invention features a composition that includes (a) bezafibrate or an analog thereof; and (b) diflunisal or an analog thereof, wherein the bezafibrate and diflunisal are present in amounts that, when administered to a patient, are sufficient to treat, prevent, or reduce a metabolic disorder (e.g., diabetes or obesity). Exemplary combinations are bezafibrate and diflunisal; bezafibrate and bismuth subsalicylate; bezafibrate and nimosulide; bezafibrate and oxaprozin; bezafibrate and diclofenac; bezafibrate and sundilac; bezafibrate and ibuprofen; clofibrate and diflunisal; clofibrate and bismuth subsalicylate; clofibrate and nimosulide; clofibrate and oxaprozin; clofibrate and diclofenac; clofibrate and sundilac; clofibrate and ibuprofen; clofibric acid and diflunisal; clofibric acid and bismuth subsalicylate; clofibric acid and nimosulide; clofibric acid and oxaprozin; clofibric acid and diclofenac; clofibric acid and sundilac; clofibric acid and ibuprofen; clinofibrate and diflunisal; clinofibrate and bismuth subsalicylate; clinofibrate and nimosulide; clinofibrate and oxaprozin; clinofibrate and diclofenac; clinofibrate and sundilac; clinofibrate and ibuprofen; gemfibrozil and diflunisal; gemfibrozil and bismuth subsalicylate; gemfibrozil and nimosulide; gemfibrozil and oxaprozin; gemfibrozil and diclofenac; gemfibrozil and sundilac; and gemfibrozil and ibuprofen.

In a second aspect, the invention features a composition that includes (a) bezafibrate or an analog thereof; and (b) cinnamic acid or an analog thereof, wherein the bezafibrate and diflunisal are present in amounts that, when administered to a patient, are sufficient to treat, prevent, or reduce a metabolic disorder.

Exemplary bezafibrate analogs are binifibrate, ciprofibrate, clinofibrate, clofibrate, clofibric acid, etofibrate, fenofibrate, or gemfibrozil.

In either of the foregoing aspects, the composition may include a third agent selected from the group consisting of sulfonylureas, non-sulfonylurea secretagogues, insulin, insulin analogs, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adenosine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diuretics, dopamine D1 receptor agonists, endopeptidase inhibitors, endothelin receptor antagonists, guanylate cyclase stimulants, phosphodiesterase V inhibitors, protein kinase inhibitors, Cdc2 kinase inhibitors, renin inhibitors, thromboxane synthase inhibitors, vasopeptidase inhibitors, vasopressin I antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholesteryl ester transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists, insulin sensitizers, lipase inhibitors, melanin-concentrating hormone receptor antagonists, nerve growth factor agonists, neuropeptide Y agonists, neuropeptide Y antagonists, SNRIs, protein tyrosine phosphatase inhibitors, and serotonin 2C receptor agonists.

The compositions of the invention may be formulated for oral administration or systemic administration.

The invention also features a method for treating, preventing, or reducing a metabolic disorder in a patient in need thereof by administering to the patient (i) bezafibrate or an analog thereof; and (ii) diflunisal or an analog thereof, wherein the bezafibrate and diflunisal are administered in amounts that together are sufficient to treat, prevent, or reduce a metabolic disorder. Exemplary combinations are bezafibrate and diflunisal; bezafibrate and bismuth subsalicylate; bezafibrate and nimosulide; bezafibrate and oxaprozin; bezafibrate and diclofenac; bezafibrate and sundilac; bezafibrate and ibuprofen; clofibrate and diflunisal; clofibrate and bismuth subsalicylate; clofibrate and nimosulide; clofibrate and oxaprozin; clofibrate and diclofenac; clofibrate and sundilac; clofibrate and ibuprofen; clofibrinc acid and diflunisal; clofibric acid and bismuth subsalicylate; clofibric acid and nimosulide; clofibric acid and oxaprozin; clofibric acid and diclofenac; clofibric acid and sundilac; clofibric acid and ibuprofen; clinofibrate and diflunisal; clinofibrate and bismuth subsalicylate; clinofibrate and nimosulide; clinofibrate and oxaprozin; clinofibrate and diclofenac; clinofibrate and sundilac; clinofibrate and ibuprofen; gemfibrozil and diflunisal; gemfibrozil and bismuth subsalicylate; gemfibrozil and nimosulide; gemfibrozil and oxaprozin; gemfibrozil and diclofenac; gemfibrozil and sundilac; and gemfibrozil and ibuprofen.

The invention also features a method for treating, preventing, or reducing a metabolic disorder in a patient in need thereof by administering to the patient (i) bezafibrate or an analog thereof; and (ii) cinnamic acid or an analog thereof, wherein the bezafibrate and cinnamic acid are administered in amounts that together are sufficient to treat, prevent, or reduce a metabolic disorder.

In either of the foregoing aspects, the patient may also be administered a third agent selected from the group consisting of sulfonylureas, non-sulfonylurea secretagogues, insulin, insulin analogs, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adenosine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diuretics, dopamine D1 receptor agonists, endopeptidase inhibitors, endothelin receptor antagonists, guanylate cyclase stimulants, phosphodiesterase V inhibitors, protein kinase inhibitors, Cdc2 kinase inhibitors, renin inhibitors, thromboxane synthase inhibitors, vasopeptidase inhibitors, vasopressin I antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholesteryl ester transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists, insulin sensitizers, lipase inhibitors, melanin-concentrating hormone receptor antagonists, nerve growth factor agonists, neuropeptide Y agonists, neuropeptide Y antagonists, SNRIs, protein tyrosine phosphatase inhibitors, and serotonin 2C receptor agonists.

The two drugs may be formulated for oral administration or systemic administration. The first and second agents are desirably administered within 10 days of each other, within 7 days of each other, within 24 hours of each other, or within 1 hour of each other.

The invention also features a kit that includes (i) bezafibrate or an analog thereof; and (ii) instructions for administering bezafibrate and cinnamic acid or an analog thereof to a patient having or at risk of having a metabolic disorder.

The invention also features a kit that includes (i) bezafibrate or an analog thereof; and (ii) instructions for administering bezafibrate and diflunisal or an analog thereof to a patient having or at risk of having a metabolic disorder.

The invention also features a kit that includes (i) diflunisal or an analog thereof; and (ii) instructions for administering diflunisal and bezafibrate or an analog thereof to a patient having or at risk of having a metabolic disorder.

The invention also features a kit that includes (i) cinnamic acid or an analog thereof; and (ii) instructions for administering cinnamic acid and bezafibrate or an analog thereof to a patient having or at risk of having a metabolic disorder.

The invention also features a kit that includes (i) a composition containing bezafibrate or an analog thereof and cinnamic acid or an analog thereof; and (ii) instructions for administering the composition to a patient having or at risk of having a metabolic disorder.

The invention also features a kit that includes (i) a composition containing bezafibrate or an analog thereof and diflunisal or an analog thereof; and (ii) instructions for administering the composition to a patient having or at risk of having a metabolic disorder.

The invention also features a kit that includes (i) bezafibrate or an analog thereof; (ii) cinnamic acid or an analog thereof; and (iii) instructions for administering bezafibrate and cinnamic acid to a patient having or at risk of having a metabolic disorder.

The invention also features a kit that includes (i) bezafibrate or an analog thereof; (ii) diflunisal or an analog thereof; and (iii) instructions for administering bezafibrate and diflunisal to a patient having or at risk of having a metabolic disorder.

The invention also features a composition that includes (a) a PPAR agonist; and (b) diflunisal or an analog thereof, wherein the PPAR agonist and diflunisal are present in amounts that, when administered to a patient, are sufficient to treat, prevent, or reduce a metabolic disorder.

The invention also features a composition that includes (a) a PPAR agonist; and (b) cinnamic acid or an analog thereof, wherein the PPAR agonist and diflunisal are present in amounts that, when administered to a patient, are sufficient to treat, prevent, or reduce a metabolic disorder.

In either of the foregoing aspects, the patient may also be administered a third agent selected from the group consisting of sulfonylureas, non-sulfonylurea secretagogues, insulin, insulin analogs, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adenosine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diuretics, dopamine D1 receptor agonists, endopeptidase inhibitors, endothelin receptor antagonists, guanylate cyclase stimulants, phosphodiesterase V inhibitors, protein kinase inhibitors, Cdc2 kinase inhibitors, renin inhibitors, thromboxane synthase inhibitors, vasopeptidase inhibitors, vasopressin I antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholesteryl ester transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists, insulin sensitizers, lipase inhibitors, melanin-concentrating hormone receptor antagonists, nerve growth factor agonists, neuropeptide Y agonists, neuropeptide Y antagonists, SNRIs, protein tyrosine phosphatase inhibitors, and serotonin 2C receptor agonists.

The compositions of the invention may be formulated for oral administration or systemic administration.

The invention also features a method for treating, preventing, or reducing a metabolic disorder in a patient in need thereof by administering to the patient (i) a PPAR agonist; and (ii) diflunisal or an analog thereof, wherein the PPARγ agonist and diflunisal are administered in amounts that together are sufficient to treat, prevent, or reduce a metabolic disorder.

The invention also features a method for treating, preventing, or reducing a metabolic disorder in a patient in need thereof by administering to the patient (i) a PPAR agonist; and (ii) cinnamic acid or an analog thereof, wherein the PPARγ agonist and cinnamic acid are administered in amounts that together are sufficient to treat, prevent, or reduce a metabolic disorder.

The invention also features a kit that includes (i) a PPAR agonist; and (ii) instructions for administering the PPAR agonist and cinnamic acid or an analog thereof to a patient having or at risk of having a metabolic disorder.

The invention features a kit that includes (i) a PPAR agonist; and (ii) instructions for administering the PPAR agonist and diflunisal or an analog thereof to a patient having or at risk of having a metabolic disorder.

The invention features a kit that includes (i) diflunisal or an analog thereof; and (ii) instructions for administering diflunisal and a PPAR agonist or an analog thereof to a patient having or at risk of having a metabolic disorder.

The invention also features a kit that includes (i) cinnamic acid or an analog thereof; and (ii) instructions for administering cinnamic acid and a PPAR agonist or an analog thereof to a patient having or at risk of having a metabolic disorder.

The invention also features a kit that includes (i) a composition containing a PPAR agonist or an analog thereof and cinnamic acid or an analog thereof; and (ii) instructions for administering the composition to a patient having or at risk of having a metabolic disorder.

The invention also features a kit that includes (i) a composition containing a PPAR agonist or an analog thereof and diflunisal or an analog thereof; and (ii) instructions for administering the composition to a patient having or at risk of having a metabolic disorder.

The invention also features a kit that includes (i) a PPAR agonist or an analog thereof; (ii) cinnamic acid or an analog thereof; and (iii) instructions for administering the PPAR agonist and cinnamic acid to a patient having or at risk of having a metabolic disorder.

The invention also features a kit that includes (i) a PPAR agonist or an analog thereof; (ii) diflunisal or an analog thereof; and (iii) instructions for administering the PPAR agonist and diflunisal to a patient having or at risk of having a metabolic disorder.

In any of the foregoing lits, the PPAR agonist is desirably a PPARγ agonist (e.g., balaglitazone, troglitazone, pioglitazone, ciglitazone, englitazone, rosiglitazone, darglitazone, englitazone, netoglitazone, KRP-297, JTT-501, NC-2100, NIP-223, MCC-555, L-764486, CS-011, GI262570, GW347845, or FK614).

The invention also features a method of treating a metabolic disorder by administering to a mammal (e.g., human) one or more agents listed in Table 1 in an amount sufficient to treat, prevent, or reduce the metabolic disorder.

For example, the mammal being treated may be administered two agents listed in Table 1 within 28 days of each other in amounts that together are sufficient to treat, prevent, or reduce the metabolic disorder. The two agents are desirably administered within 14 days of each other, more desirably within seven days of each other, and even more desirably within twenty-four hours of each other, or even simultaneously (i.e., concomitantly). If desired, either one of the two agents may be administered in low dosage.

Optionally, the mammal being treated may receive an additional therapeutic regimen. If a therapeutic agent is employed as the additional therapeutic regimen, the agent or agents from Table 1 and the additional agent are present in amounts that, when administered to a mammal, are together sufficient to treat, prevent, or reduce a metabolic disorder. The additional agent may be selected from the group consisting of sulfonylureas, non-sulfonylurea secretagogues, insulin, insulin analogs, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adenosine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diuretics, dopamine D1 receptor agonists, endopeptidase inhibitors, endothelin receptor antagonists, guanylate cyclase stimulants, phosphodiesterase V inhibitors, protein kinase inhibitors, Cdc2 kinase inhibitors, renin inhibitors, thromboxane synthase inhibitors, vasopeptidase inhibitors, vasopressin 1 antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholesteryl ester transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists, insulin sensitizers, lipase inhibitors, melanin-concentrating hormone receptor antagonists, nerve growth factor agonists, neuropeptide Y agonists, neuropeptide Y antagonists, SNRIs, protein tyrosine phosphatase inhibitors, and serotonin 2C receptor agonists.

If desired, more than one therapeutic agent may be used with any of the agents listed in Table 1.

TABLE 1

| | | | | | |
|---|---|---|---|---|---|
| 5-10-Dihydro-5-10-Dimethylphenazine | Calcium Chloride | 5-Hydroxytryptophan (e.g., DL form) | Indocyanine Green | Mono-Butyl Maleate | Succinylcholine |
| Acemetacin | Candesartan (e.g., cilexetil salt) | Dopamine (e.g., hydrochloride) | Indomethacin | Nefopam | Sulfaguanidine |
| Acenocoumarol | Captopril | Doxapram (e.g., hydrochloride salt) | Inulin | Nimesulide | Sulfamethizole |
| Acetaminophen | Carbamazepine | Doxycycline | Invertase | Nitroxoline | Sulfasomidine |
| Acetazolamide | Carbinoxamine (e.g., maleate salt) | Doxylamine (e.g., succinate salt) | Iopanoic Acid | Norepinephrine (e.g., bitartrate salt) | Suprofen |
| Acetohexamide | Carisoprodol | Dyclonine (e.g., hydrochloride salt) | Iophenoxic Acid | Olanzapine | Tadalafil |
| Acetohydroxamic Acid | Cefamandole (e.g., nafate salt) | Enalaprilat | Iopromide | Oleandomycin | Tannic Acid |
| Acetrizoate (e.g., sodium salt) | Cefpodoxime Proxetil | Epinephrine (e.g., bitartrate salt) | Isoproterenol (e.g., sulfate salt) | Orphenadrine (e.g., citrate salt) | Telmisartan |
| Acetylcholine (e.g., chloride salt) | Ciclopirox | Ergoloid Mesylates | Isotretinoin | Oxaprozin | Terbutaline (e.g., sulfate salt) |
| Acetyldigitoxin | Cinnamic Acid | Ethopropazine (e.g., hydrochloride salt) | Ketoconazole | Oxybutynin (e.g., chloride salt) | Tetrahydrozoline (e.g., hydrochloride salt) |
| Alachlor | Clenbuterol (e.g., hydrochloride salt) | Etoposide | Ketotifen (e.g., fumarate salt) | Oxymetazoline (e.g., hydrochloride salt) | Tinidazole |
| Albuterol (Salbutamol) (e.g., sulfate salt) | Clioquinol | Eucalyptol | Lamivudine | Pergolide (e.g., mesylate salt) | Tioconazole |
| Alprenolol | Copper bis-3,5-diisopropylsalicylate | Evans Blue | Lead Dimethyldithiocarbamate | Phenacemide | Tolazoline (e.g., hydrochloride salt) |
| Amantadine (e.g., hydrochloride salt) | Cupric Chloride | Exemestane | Leflunomide | Phenindione | Tolfenamic acid |
| Ametryn | Dexibuprofen | Flunixin (e.g., meglumine salt) | Levocabastine (e.g., hydrochloride salt) | Phensuximide | Tretinoin |
| Ammonium Chloride | Diacerein | Fumaric Acid Monoethyl Ester | Levonordefrin | Phenylbutazone | Triamterene |

TABLE 1-continued

| | | | | | |
|---|---|---|---|---|---|
| Arbutin | Diallyl Maleate | Gemfibrozil | Loxapine (e.g., hydrochloride salt) | Phenylephrine (e.g., hydrochloride salt) | Triflupromazine (e.g., hydrochloride salt) |
| Artemether | Diatrizoate (e.g., sodium salt) | Genistein | Manganese Sulfate | Phenylpropanolamine (e.g. hydrochloride salt) | Tulobuterol (e.g., hydrochloride salt) |
| Aspartic Acid Hydroxamate | Diclofenac (e.g., sodium salt) | Geranyl Acetate | Mebhydroline (e.g., 1,5-Naphthalenedisulfonate salt) | Phenytoin | Vincamine |
| Atrazine | Dicloxacillin (e.g., sodium salt) | Glutamic Acid Hydrochloride | Meclofenoxate | Pilocarpine (e.g., hydrochloride salt) | Warfarin |
| Azathioprine | Diflunisal | Guaiacol | Mefenamic Acid | Prazosin (e.g., hydrochloride salt) | Xylazine (e.g., hydrochloride salt) |
| Bamethan | Digitoxin | Guanfacine (e.g., hydrochloride salt) | Meloxicam | Promethazine (e.g., hydrochloride salt) | Zaprinast |
| Benzbromarone | Dimenhydrinate | Hexylcaine (e.g., hydrochloride salt) | Melphalan | Prostaglandin (e.g., prostaglandin E) | |
| Bezafibrate | Dimethyl Fumarate | Homatropine Methylbromide | Mercaptoethanol | Pyrilamine (e.g., maleate salt) | |
| Bismuth Subsalicylate | Diphemanil Methylsufate | Hydroxocobalamin | Metaproterenol (e.g., hemisulfate salt) | Quinacrine | |
| Bopindolol | Diphenhydramine (e.g., hydrochloride salt) | Hydroxypropyl Cellulose | Methacholine (e.g., chloride or bromide salt) | Ritodrine (e.g., hydrochloride salt) | |
| Brimonidine | Diphenidol (e.g., hydrochloride salt) | Ibudilast | Methdilazine | RO-20-1724 | |
| Brompheniramine (e.g., maleate salt) | Dipivefrin (e.g., hydrochloride salt) | Ibuprofen | Methyl Linoleate | Rolipram | |
| Calcitriol | Dirithromycin | Imipramine (e.g., hydrochloride salt) | Methylergonovine (e.g., maleate salt) | Spectinomycin | |

If the mammal is administered more than one agent, the different agents may be admixed together in a single formulation. When administered in separate formulations, the agents may be administered simultaneously or within 14 days, 7 days, or 1 day of each other. These agents may or may not be administered by the same route of administration (e.g., oral, intravenous, intramuscular, ophthalmic, topical, dermal, sub-cutaneous, and rectal). Optionally, the additional therapeutic regimen may involve a lifestyle change, including the adoption of a low-fat diet or low-sodium diet, stress management, physical exercise, reduction in alcohol intake, or reduction in smoking.

In a further aspect, the present invention features a kit that includes any one of the agents listed in Table 1 and instructions for its administration to a patient having or at risk of having a metabolic disorder. Optionally, the kit contains two, three, four, or more than four agents from Table 1 that may or may not be admixed in the same formulation. This kit may also contain instructions for administering this agent with a second agent listed in Table 1.

The invention also features a kit that includes (a) one, two, three, or more agents listed in Table 1 and (b) one or more of the following agents: a sulfonylurea, non-sulfonylurea secretagogue, insulin, insulin analog, glucagon-like peptide, exendin-4, YM178, FK614, dipeptidyl peptidase IV inhibitor, biguanide, thiazalidinedione, alpha-glucosidase inhibitor, immunosuppressant, immunomodulator, angiotensin converting enzyme (ACE) inhibitor, angiotensin II receptor blocker, or antioxidant. The kit also includes instructions for administering these agents to a patient having or at risk of having a metabolic disorder.

Alternatively, the kit of the invention may contain one, two, three, or more agent listed in Table 1 or any one of the following agents: a sulfonylurea, non-sulfonylurea secretagogue, insulin, insulin analog, glucagon-like peptide, exendin-4, YM178, FK614, dipeptidyl peptidase IV inhibitor, biguanide, thiazalidinedione, alpha-glucosidase inhibitor, immunosuppressant, immunomodulator, angiotensin converting enzyme (ACE) inhibitor, angiotensin II receptor blocker, and antioxidant, as well as instructions for administering these two agents together to a patient having or at risk of having a metabolic disorder.

The invention also features a method of identifying a combination of agents useful for the treatment, prevention, or reduction of a metabolic disorder, involving the steps of: (a) contacting cells with an agent listed in Table 1 and a candidate compound; and (b) determining whether this combination of agents reduces glucose levels relative to cells contacted only with the agent from Table 1 but not contacted with the candidate compound. A reduction in glucose levels identifies the combination as being useful for the treatment, prevention, or reduction of a metabolic disorder. Glucose levels may be reduced, for example, by altering insulin signaling (therefore increasing glucose uptake into cells and subsequent storage or metabolism, for example), altering glucose transporter activity (e.g., increasing GLUT4 expression, translocation, or intrinsic activity), increasing the amount of insulin-sensitive tissue (e.g., by increasing adipocyte or muscle cell differentiation), or altering gene transcription in adipocytes or muscle cells (e.g., altered secretion of factors from adipocytes and expression of metabolic pathway genes).

For example, the screening method for identifying a useful therapeutic combination involves the steps of: (a) contacting cells with an agent listed in Table 1 and a candidate compound; and (b) determining whether this combination of agents alters insulin signaling such that glucose levels are reduced relative to cells contacted with the agent from Table 1 but not contacted with the candidate compound. An alteration in insulin signaling that reduces glucose levels identifies the combination as being useful for the treatment, prevention, or reduction of a metabolic disorder.

Mammalian (e.g., human) cells may be employed in any of the screening methods described herein. Particularly useful cells are muscle cells, intestinal cells, adipocytes, liver cells, and pancreatic cells. Optionally, these cells have an alteration in insulin signaling activity such that glucose levels are increased. Such a reduction in glucose levels may result from an increase in insulin production, an increase in insulin secretion, an increase in glucose uptake by peripheral tissues, a reduction in hepatic glucose production, or a reduction in the absorption of carbohydrates from the intestines.

Analogs of any of the compounds listed in Table 1 may be used in any of the methods, kits, and compositions of the invention. Such analogs include any agent from the same chemical class, mechanistic class, or therapeutic class as those listed in Table 2.

TABLE 2

| name | chemical class | mechanistic class | therapeutic class |
|---|---|---|---|
| 5-10-dihydro-5-10-dimethylphenazine | phenothiazine | | |
| 5-hydroxytryptophan (e.g., dl form) | | intermediate metabolite of lt in the production of serotonin | anti-depressant |
| acemetacin | indomethacin derivative | cyclooxegynase inhibitor | anti-inflammatory agents non-steroidal |
| acenocoumarol | heterocyclic coumarin | anticoagulant | thromboembolism atrial fibrillation pulmonary embolism |
| acetaminophen | sodium sulfate | blocks cyclooxygenase (prostaglandin formation) | NSAID |
| acetazolamide | sulfa-based | carbonic anhydrase inhibitor | anti-epileptic |
| acetohexamide | sulfonylureas | stimulate beta cell insulin secretion | oral hypoglycemic drugs |
| acetohydroxamic acid | | specific inhibitor of urease | antibacterial |
| acetrizoate (e.g., sodium salt) | acetrizoic acid | iodinated radiographic contrast medium used in hysterosalpingography | |
| acetylcholine (e.g., chloride salt) | | mixed cholinergic agonist | neurotransmitter |
| acetyldigitoxin | | sodium potassium atpase | inotropic congestive heart failure |
| alachlor | acetamide | | herbicide |
| albuterol (salbutamol) sulfate | ethanolamine | beta agonist | bronchodilator |
| alprenolol | proponalamine | andrenergic beta antagonist | antihypertensive, anti-anginal, and anti-arrhythmic agent |
| amantadine (e.g., hydrochloride salt) | | | antiparkinson |
| ametryn | triazine | | herbicide |
| ammonium chloride | ammonia derivative | | diuretics, expectorants |
| arbutin | | tyrosinase inhibitor | dermatological |
| artemether | artemisinins | | anti-malarial |
| aspartic acid hydroxamate | asperigine | | antineoplastic agents antiviral agents |
| Atrazine | triazine | selective triazine herbicide | herbicide |
| azathioprine | heterocyclic | | immunosuppressive |
| bamethan | | | vasodilator |
| benzbromarone | benzofuran | acts by increasing uric acid clearance | antigout |
| bezafibrate | butyrate | lowers cholesterol and triglycerides | antilipemic, cholesterol lowering |
| bismuth subsalicylate | bismuth salt | increases intracellular Ca2+, MAP-kinase activity, and cell proliferation in normal human gastric mucous epithelial cells | anti-diarrheal |
| bopindolol | beta antagonist — antihypertensive | | |
| brimonidine | | alpha-adrenergic receptor agonist | anti-glaucoma |
| brompheniramine maleate | pheniramine | histamine H1 antagonist | anti-allergic agent |
| calcitriol | vitamin D analog | calcium channel agonists | dermatological |
| calcium chloride | | | dietary supplement |
| candesartan (e.g., cilexetil salt) | benzimidazole | TL-type angiotensin II receptor antagonist | antihypertensive |
| captopril | mercaptan | angiotensin-converting enzyme inhibitors | antihypertensive |
| carbamazepine | iminostilbene derivative | | anticonvulsant |
| carbinoxamine (e.g., maleate salt) | | histamine H1 antagonist | antihistamine |
| carisoprodol | carbamic acid | | sedative/muscle relaxent |
| cefamandole (e.g., nafate salt) | cephalosporins | cell wall synthesis inhibitor | antibiotic |
| cefpodoxime proxetil | cephalosporins | | antibiotic |
| ciclopirox | hydroxypyridone | fungicide | topical antifungal |
| cinnamic acid | cinnamate | | flavoring, coloring |

TABLE 2-continued

| name | chemical class | mechanistic class | therapeutic class |
|---|---|---|---|
| clenbuterol hydrochloride | beta-2-symphatomimetic | beta agonist | anticatabolic |
| clioquinol | 8-hydroxyquinoline derivative | | antifungal, amoebicides |
| copper bis-3,5-diisopropylsalicylate | salicyclic acid | | antineoplastic, hypoglycemic agent |
| cupric chloride | mineral | | antifungal |
| dexibuprofen | single-enantiomer form of ibuprofen | inhibits prostaglandin synthesis | NSAID |
| diacerein | anthraquinones | | NSAID |
| diallyl maleate | mallic acid | | plastics additive |
| diatrizoate (e.g., sodium salt) | | | x-ray contrast medium |
| diclofenac sodium | benzeneacetic acid | | NSAID |
| dicloxacillin (e.g., sodium salt) | penicillin derivative/beta-lactam | inhibits bacterial cell wall synthesis | antibiotic |
| diflunisal | salicylate derivative | cyclooxygenase inhibitors | NSAID |
| digitoxin | cardiac glycoside | inhibits Na+/K+ ATPase cell membrane transport complex | inotropic cardiovascular agent, congestive heart failure |
| dimenhydrinate | diphenhydramine and chlorotheophylline | histamine H1 antagonists | vertigo agent |
| dimethyl fumarate | fumarate | | anti-psoriatic |
| diphemanil methylsufate | synthetic quaternary ammonium compound | anti-muscarinic agent | |
| diphenhydramine (e.g., hydrochloride salt) | ethanolamine | histamine H1 receptor antagonist | antihistamine |
| diphenidol (e.g., hydrochloride salt) | | muscarinic antagonist | anti-nausea, vomiting, dizziness |
| dipivefrin hydrochloride | prodrug of epinephrine | bronchodialator | anti-glaucoma |
| dirithromycin | | inhibits bacterial protein synthesis at the 50s ribosome (macrolide) | antibacterial |
| dopamine (e.g., hydrochloride) | | neurotransmitter | antidepressant |
| doxapram (e.g., hydrochloride salt) | | respiratory stimulant | acute hypercarnic respiratory failure |
| doxycycline | tetracycline derivative | protein-synthesis-inhibitor | antibiotic |
| doxylamine (e.g., succinate salt) | butanedioic acid | antihistamine-H1/serotonin-secretion-inhibitor | allergic rhinitis |
| dyclonine (e.g., hydrochloride salt) | | nerve sodium-permeability-inhibitor | pain reliever |
| enalaprilat | oligopeptide | ACE inhibitor | antihypertensive |
| epinephrine bitartrate | hormone | induces cyclic AMP | stimulant, asthma |
| ergoloid mesylates | dihydroergotoxine | adrenergic alpha-antagonists | Alzheimer's disease |
| ethopropazine (e.g., hydrochloride salt) | phenothiazine | Antidyskinetic | Parkinson's disease |
| etoposide | glucoside | topoisomerase II inhibitor | antineoplastic agent, phytogenic |
| eucalyptol | cyclohexanols | | local anti-infective agent |
| evans blue | azo dye | | diagnostic for blood volume determination |
| exemestane | androstadiene | aromatase antagonist/inhibitor | antineoplastic agent |
| flunixin meglumine | clinixin derivative | prostaglandin antagonist | NSAID |
| fumaric acid monoethyl ester | fumarate | | anti-psoriatic |
| gemfibrozil | pentonoic acid | lowers elevated serum lipids primarily by decreasing serum triglycerides | lipid lowering |
| genistein | isoflavone | | angiogenesis blocker |
| geranyl acetate | isoflavone | | antineoplastic agent |
| glutamic acid hydrochloride | amino acid | amino acid | |
| guaiacol | phenol | | disinfectant, expectorant |
| guanfacine (e.g., hydrochloride salt) | acetamide | α2-adrenoceptor agonist | antihypertensive |
| hexylcaine (e.g., hydrochloride salt) | benzoic acid derivitive | | topical anesthetic |
| homatropine methylbromide | tropine ester of mandelic acid | | antispasmodic and inhibitor of secretions |
| hydroxocobalamin | vitamin B12 | inhibits vitamin B12 deficiency | synthetic vitamin B12 |
| hydroxypropyl cellulose | cellulose | Mechanical | topical artificial tear |
| ibudilast | pyridine | phosphodiesterase iv inhibitor | anti-asthma |
| ibuprofen | phenylpropionates | cyclooxygenase inhibitor | NSAID |
| imipramine (e.g., hydrochloride salt) | dibenzazepine | blocks ne uptake at adrenergic nerve endings | antidepressant |
| indocyanine green | tricarbocyanine | infrared absorbance | diagnostic for angiography |
| indomethacin | indole | cyclooxygenase inhibitor | NSAID |

TABLE 2-continued

| name | chemical class | mechanistic class | therapeutic class |
|---|---|---|---|
| inulin | oligosaccharide | | diagnostic for kidney health; probiotic; dietary fiber |
| invertase | beta-fructofuranosidase | hydrolysis of the terminal nonreducing beta-fructofuranoside residues in beta-fructofuranosides | enzyme |
| iopanoic acid | | radiopaque compound | antihyperthyroid agent; x-ray contrast medium |
| iophenoxic acid | | radiopaque compound | x-ray contrast medium |
| iopromide | benzoic acid derivitive | | |
| isoproterenol (e.g., sulfate salt) | amine | beta adrenergic agonist | inotropic agent |
| isoproterenol sulfate | analog of epinephrine | sympathomimetic, direct-acting | beta agonist |
| isotretinoin | retinoid | | acne vulgaris |
| ketoconazole | azole | | antifungal |
| ketotifen fumarate | cycloheptathiophene | H1 receptor antagonist | asthma, rhinitis, skin allergies, and anaphylaxis. |
| lamivudine | deoxyribonucleoside | reverse transcriptase inhibitor | anti-HIV treatment |
| lead dimethyldithiocarbamate | carbamic acid | | rubber accelerator |
| leflunomide | oxazole | inhibits dihydroorotate dehydrogenase | DMARD |
| levocabastine (e.g., hydrochloride salt) | | antihistaminic, H1-receptor; ophthalmic | antiallergic; opthalmic |
| levonordefrin | norepinephrine derivative | stimulates alpha- and beta- adrenergic systems | vasoconstrictor, local anesthetic for dentistry |
| loxapine (e.g., hydrochloride salt) | tricyclic dibenzoxazepine | | antipsychotic agent |
| manganese sulfate | sulfate | | |
| mebhydroline (e.g., 1,5-naphthalenedisulfonate salt) | aralkylamine carboline | histamine H1 antagonists | antihistamine |
| mebhydroline 1,5-naphthalenedisulfonate salt | naphthalenesulfonates | | |
| meclofenoxate | aminoalcohol | | stimulant |
| mefenamic acid | anthranilic acid | cyclooxygenase inhibitor | NSAID |
| meloxicam | oxicam derivative | cyclooxygenase inhibitor | NSAID |
| melphalan | nitrogen mustard compound | alkylating antineoplastic not completely understood | antineoplastic |
| mercaptoethanol | sulfhydryl compound | reducing agent | biochem reagent |
| metaproterenol (e.g., hemisulfate salt) | ethanolamine | beta-adrenergic agonist | treatment of asthma and bronchospams |
| metaproterenol hemisulfate salt | synthetic sympathomimetic amine | beta agonist | bronchodilator |
| methacholine (e.g., bromide salt) | quarternary ammonium | muscarinic agonist | parasympathomimetic bronchoconstrictor agent |
| methacholine (e.g., chloride salt) | quarternary ammonium | muscarinic agonist | parasympathomimetic bronchoconstrictor agent |
| methdilazine | phenothiazine | antihistamine h1 receptor agonist | allergies, antipsychotic |
| methyl linoleate | linoleic acid | antioxidant | flavoring agent |
| methylergonovine (e.g., maleate salt) | ergot alkyloid homolog | oxytocic | obstetrics, to induce labor |
| mono-butyl maleate | maleate ester | fumarate sar | anti-inflammatory |
| nefopam | oxazocine | | analgesic |
| nimesulide | sulfonanilide | COX-2 inhibitor | NSAID |
| nitroxoline | chelating agent | bactericidal chelation | antibacterial, antifungal |
| norepinephrine bitartrate | catecholamine | alpha adrenergic agonist | vasoconstrictor |
| olanzapine | benzodiazepine | antiemetic | anti-nausea |
| oleandomycin | macrolide | binds to 23s rrna or 50s subunit inhibits translocation or trna, inhibits peptidyl transferase interfere w/formation of 50s unit inhibit protein synthesis | antibiotic |
| orphenadrine (e.g., citrate salt) | ethylamine | muscarinic antagonist | drug-induced parkinsonism |
| oxaprozin | propionic acid derivative | prostaglandin inhibitor | NSAID |
| oxybutynin (e.g., chloride salt) | mandelic acid | competitive antagonist of acetylcholine at postganglionic muscarinic receptors, | antispasmodic, urinary tract |
| oxymetazoline (e.g., hydrochloride salt) | imidazole | adrenergic alpha-agonists, direct acting sympathomimetic | vasoconstrictor to relieve nasal congestion |
| pergolide (e.g., mesylate salt) | ergoline | dopamine agonist | Parkinson's disease |
| phenacemide | urea deriviative | | anti-epileptic drug |
| phenindione | indandione derivative | anti-vitamin K agent | anticoagulent |
| phensuximide | succinimide | | anticonvulsant |

TABLE 2-continued

| name | chemical class | mechanistic class | therapeutic class |
|---|---|---|---|
| phenylbutazone | pyrazole | cyclooxegenase inhibitor | ankylosing spondylitis, rheumatoid arthritis |
| phenylephrine (e.g., hydrochloride salt) | ethanolamine | alpha-adrenergic agonist | ophthalmic examinations |
| phenylpropanolamine (e.g., hydrochloride salt) | propanolamine | adrenergic alpha-agonists | nasal vasoconstrictor and an appetite depressant. |
| phenytoin | barbiturates | | anticonvulsant |
| pilocarpine (e.g., hydrochloride salt) | lactone imdiazole | acetylcholine agonist | antiglaucoma agent |
| prazosin (e.g., hydrochloride salt) | quinazoline piperazine | alpha-adrenergic receptor antagonist | antihypertensive |
| promethazine (e.g., hydrochloride salt) | phenathiazine | histamine H1 receptor antagonists | antihistamine |
| prostaglandin e | carboxylic acid | prostaglandin | vasodilator |
| pyrilamine (e.g., maleate salt) | | histamine H1 receptor antagonists | antihistamine |
| quinacrine | | phospholipase inhibitor | anti-malarial |
| ritodrine hydrochloride | catecholamine | beta agonist | relaxant |
| RO-20-1724 | polyphenyl imidazole | camp phosphodiesterase inhibitor | NSAID |
| rolipram | polyphenyl pyrrole | phosphodiesterase IV inhibitor | NSAID, antidepressant, anti-parkinsonian, tranquilizer |
| spectinomycin | | antibiotic | bacterial infection |
| succinylcholine | | acetylcholine agonist | muscle relaxant |
| sulfaguanidine | sulfonamide derivative | anti-bacterial agent | antibiotic |
| sulfamethizole | sulfa drug | antibiotic | urinary-tract infections |
| sulfasomidine | sulfa drug | antibiotic | urinary-tract infections |
| suprofen | thiopene ketoacid | Prostaglandin-antagonist/nsaid | analgesics |
| tadalafil | PDEi | phosphodiesterase inhibitor | vasodilator |
| tannic acid | glycoside | | astringent |
| telmisartan | carboxylic acid | ACE inhibitor | antihypertensive (angio 2 receptor antagonist) |
| terbutaline (e.g., sulfate salt) | | bronchodilator | asthma |
| tetrahydrozoline (e.g., hydrochloride salt) | naphthalene imidazole | HMG-coA reductase inhibitor/sympathomimetics-alpha | conjunctival congestion |
| tinidazole | imidazole | | antiprotozoal |
| tioconazole | imidazole | phenolic antioxitant | antifungal |
| tolazoline (e.g., hydrochloride salt) | imidazole | vasodilator | peripheral vascular-disorders |
| tolfenamic acid | anthranillic acid | calcium channel blocker | NSAID |
| tretinoin | trans-retinoic acid | lysosomal labilization | keratolytic |
| triamterene | triaminopteridine | aldosterone receptor antagonist | diuretic |
| triflupromazine (e.g., hydrochloride salt) | phenathiazine | dopamine receptor antagonist | antipsychotic |
| tulobuterol hydrochloride | benzyl alcohol | beta agonist | bronchiodilator |
| vincamine | | vasodialator | tinnitus anti-ischemic |
| warfarin | coumarin derivative | anti-vitamin k agent | anticoagulant |
| xylazine (e.g., hydrochloride salt) | thaizine | alpha-2-adrenergic agonist | analgesic |
| zaprinast | cyclic amidine | phosphodiesterase v inhibitor | vasodilator |

By "treating, reducing, or preventing a metabolic disorder" is meant ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

A patient who is being treated for a metabolic disorder is one who a medical practitioner has diagnosed as having such a condition. Diagnosis may be performed by any suitable means, such as those described herein. A patient in whom the development of diabetes or obesity is being prevented may or may not have received such a diagnosis. One in the art will understand that patients of the invention may have been subjected to standard tests or may have been identified, without examination, as one at high risk due to the presence of one or more risk factors, such as family history, obesity, particular ethnicity (e.g., African Americans and Hispanic Americans), gestational diabetes or delivering a baby that weighs more than nine pounds, hypertension, having a pathological condition predisposing to obesity or diabetes, high blood levels of triglycerides, high blood levels of cholesterol, presence of molecular markers (e.g., presence of autoantibodies), and age (over 45 years of age). An individual is considered obese when their weight is 20% (25% in women) or more over the maximum weight desirable for their height. An adult who is more than 100 pounds overweight, is considered to be morbidly obese. Obesity is also defined as a body mass index (BMI) over 30 kg/m$^2$.

By "a metabolic disorder" is meant any pathological condition resulting from an alteration in a patient's metabolism. Such disorders include those resulting from an alteration in glucose homeostasis resulting, for example, in hyperglycemia. According to this invention, an alteration in glucose levels is typically an increase in glucose levels by at least 5%, 10%, 20%, 30%, 40%, 50%, 60%, 70%, 80%, 90%, or even 100% relative to such levels in a healthy individual. Metabolic disorders include obesity and diabetes (e.g., diabetes type I, diabetes type II, MODY, and gestational diabetes), satiety, and endocrine deficiencies of aging.

By "reducing glucose levels" is meant reducing the level of glucose by at least 10%, 20%, 30%, 40%, 50%, 60%, 70%, 80%, 90%, 95%, or 100% relative to an untreated control. Desirably, glucose levels are reduced to normoglycemic levels, i.e., between 150 to 60 mg/dL, between 140 to 70 mg/dL, between 130 to 70 mg/dL, between 125 to 80 mg/dL, and preferably between 120 to 80 mg/dL. Such reduction in glucose levels may be obtained by increasing any one of the biological activities associated with the clearance of glucose from the blood. Accordingly, an agent having the ability to reduce glucose levels may increase insulin production, secretion, or action. Insulin action may be increased, for example, by increasing glucose uptake by peripheral tissues and/or by reducing hepatic glucose production. Alternatively, the agent of the invention may reduce the absorption of carbohydrates from the intestines, alter glucose transporter activity (e.g., by increasing GLUT4 expression, intrinsic activity, or translocation), increase the amount of insulin-sensitive tissue (e.g., by increasing muscle cell or adipocyte cell differentiation), or alter gene transcription in adipocytes or muscle cells (e.g., altered secretion of factors from adipocytes expression of metabolic pathway genes). Desirably, the agent of the invention increases more than one of the activities associated with the clearance of glucose.

By "alter insulin signaling pathway such that glucose levels are reduced" is meant to alter (by increasing or reducing) any one of the activities involved in insulin signaling such that the overall result is an increase in the clearance of glucose from plasma. For example, the agent of the invention alters the insulin signaling pathway causing an increase in insulin production, secretion, or action, an increase in glucose uptake by peripheral tissues, a reduction in hepatic glucose production, or a reduction in the absorption of carbohydrates from the intestines.

By "patient" is meant any animal (e.g., a human), including horses, dogs, cats, pigs, goats, rabbits, hamsters, monkeys, guinea pigs, rats, mice, lizards, snakes, sheep, cattle, fish, and birds.

By "an amount sufficient" is meant the amount of a compound, alone or in combination with another therapeutic regimen, required to treat, prevent, or reduce a metabolic disorder such as diabetes in a clinically relevant manner. A sufficient amount of an active compound used to practice the present invention for therapeutic treatment of conditions caused by or contributing to diabetes varies depending upon the manner of administration, the age, body weight, and general health of the mammal or patient. Ultimately, the prescribers will decide the appropriate amount and dosage regimen. Additionally, an effective amount may be an amount of compound in the combination of the invention that is safe and efficacious in the treatment of a patient having a metabolic disorder such as diabetes over each agent alone as determined and approved by a regulatory authority (such as the U.S. Food and Drug Administration).

By "more effective" is meant that a treatment exhibits greater efficacy, or is less toxic, safer, more convenient, or less expensive than another treatment with which it is being compared. Efficacy may be measured by a skilled practitioner using any standard method that is appropriate for a given indication.

By "low dosage" is meant at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that reduces glucose levels and that is formulated for administration by inhalation will differ from a low dosage of the same agent formulated for oral administration.

By a "high dosage" is meant at least 5% (e.g., at least 10%, 20%, 50%, 100%, 200%, or even 300%) more than the highest standard recommended dosage of a particular compound for treatment of any human disease or condition.

Compounds useful in the invention include those described herein in any of their pharmaceutically acceptable forms, including isomers such as diastereomers and enantiomers, salts, esters, solvates, and polymorphs thereof, as well as racemic mixtures and pure isomers of the compounds described herein.

By "corticosteroid" is meant any naturally occurring or synthetic compound characterized by a hydrogenated cyclopentanoperhydrophenanthrene ring system and having immunosuppressive and/or anti-inflammatory activity. Naturally occurring corticosteroids are generally produced by the adrenal cortex. Synthetic corticosteroids may be halogenated. Exemplary corticosteroids are provided herein.

By "non-steroidal immunophilin-dependent immunosuppressant" or "NsIDI" is meant any non-steroidal agent that decreases proinflammatory cytokine production or secretion, binds an immunophilin, or causes a down regulation of the proinflammatory reaction. NsIDIs include calcineurin inhibitors, such as cyclosporine, tacrolimus, ascomycin, pimecrolimus, as well as other agents (peptides, peptide fragments, chemically modified peptides, or peptide mimetics) that inhibit the phosphatase activity of calcineurin. NsIDIs also include rapamycin (sirolimus) and everolimus, which bind to an FK506-binding protein, FKBP-12, and block antigen-induced proliferation of white blood cells and cytokine secretion.

By "small molecule immunomodulator" is meant a non-steroidal, non-NsIDI compound that decreases proinflammatory cytokine production or secretion, causes a down regulation of the proinflammatory reaction, or otherwise modulates the immune system in an immunophilin-independent manner.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups.

By "$C_{1-4}$ alkyl" is meant a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups. $C_{1-4}$ alkyls include, without limitation, methyl, ethyl, n-propyl, isopropyl, cyclopropyl, cyclopropylmethyl, n-butyl, iso-butyl, sec-butyl, tert-butyl, and cyclobutyl.

By "halogen" is meant bromine, chlorine, iodine, or fluorine.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

Other features and advantages of the invention will be apparent from the detailed description and from the claims.

$$HOMA = \frac{fasting\ serum\ glucose \times fasting\ serum\ insulin}{22.5}$$

Pio=pioglitazone; Bez=bezafibrate; DF=diflunisal; HF=high fat.

Figure 2:
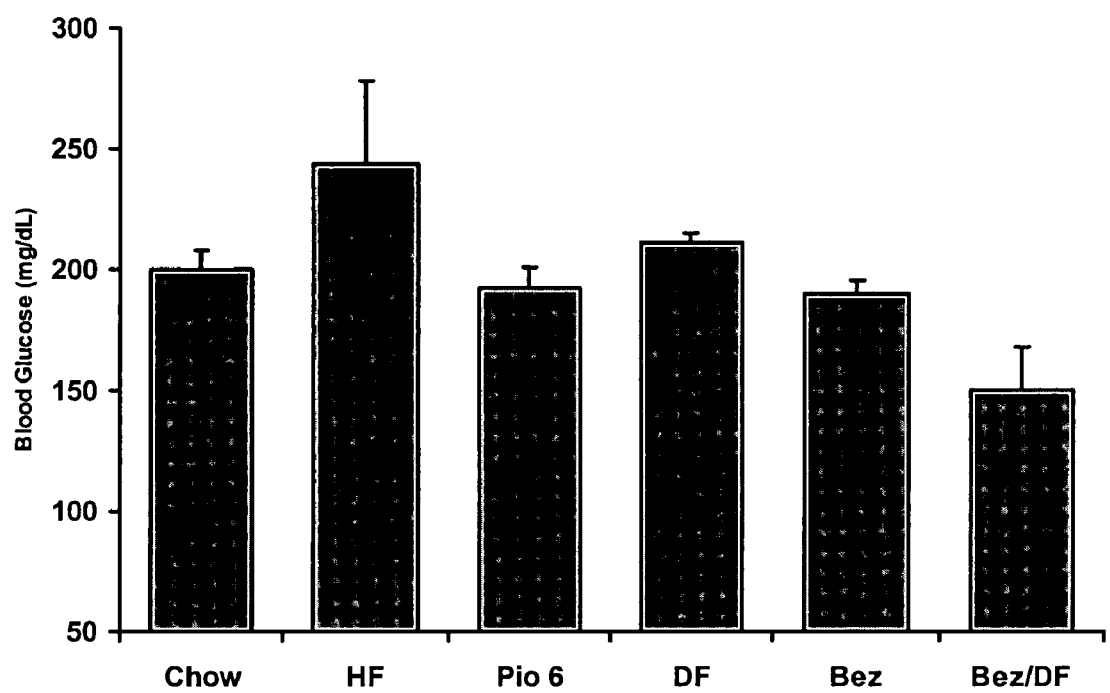

FIG. 2 is a graph showing blood glucose levels in male Sprague Dawley rats. Insulin resistance was induced by four weeks of high fat feeding (60% of calories derived from fat). Drug treatment began one week after initiation of high fat diet. Drugs were administered daily, by oral gavage for a three week period. Following the three weeks of treatment, animals were fasted for five hours and anesthetized, and blood collected from the inferior vena cava.

Figure 3:
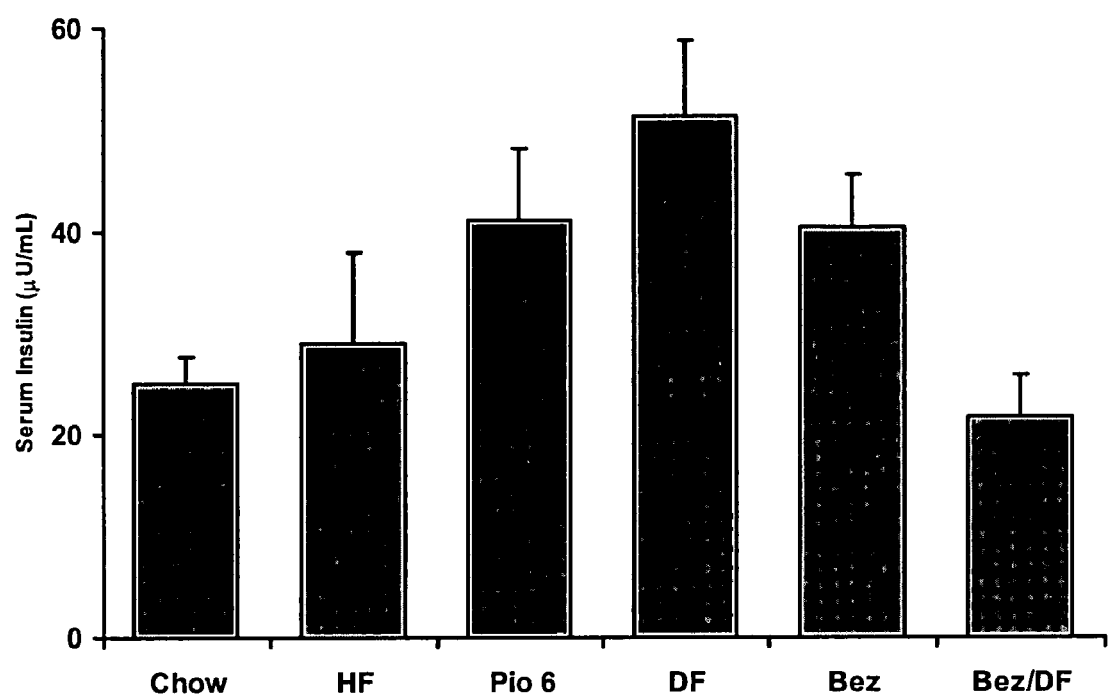

FIG. 3 is a graph showing blood serum insulin levels in male Sprague Dawley rats. Insulin resistance was induced by four weeks of high fat feeding (60% of calories derived from fat). Drug treatment began one week after initiation of high fat diet. Drugs were administered daily, by oral gavage for a three week period. Following the three weeks of treatment, animals were fasted for five hours and anesthetized, and blood collected from the inferior vena cava.

DETAILED DESCRIPTION

We have discovered compounds that the certain bezafibrate-containing combinations have in vitro and in vivo activities that suggest that these combinations may be useful for treating a patient that has been diagnosed with or is at risk of having a metabolic disorder. Optionally, analogs of these agents may be employed. In the case of diabetes and obesity, for example, such administration may reduce the levels of glucose, reduce levels of LDL-cholesterol, increase the levels of HDL-cholesterol, result in a more favorable ratio between LDL-cholesterol and HDL-cholesterol, reduce the triglyceride values, or reduce serum levels of CRP (C-reactive protein). The ability of the agent to cause the clearance of glucose may be attributed, for example, to its ability to increase insulin production, secretion, or action (e.g., stimulation of glucose uptake by peripheral tissues and/or reduction in hepatic glucose production), reduce the absorption of carbohydrates from the intestines, alter glucose transporter activity (e.g., by increasing GLUT4 expression, intrinsic activity, or translocation), increase the level of insulin-sensitive tissue (e.g., by increasing adipocyte or muscle cell differentiation), or alter gene transcription in adipocytes or muscle cells (e.g., altered secretion of factors from adipocytes and expression of metabolic pathway genes).

In one example, we propose that the administration of bezafibrate and cinnamic acid to a patient having a metabolic disorder such as diabetes within 14 days of each other will treat, prevent, or reduce the metabolic disorder. In another example, the administration of bezafibrate and diflunisal to the patient within 14 days of each other will also treat, prevent, or reduce the metabolic disorder. The two agents are desirably administered within 10 days of each other, more desirably within seven days of each other, and even more desirably within twenty-four hours of each other, one hour of each other, or even simultaneously (i.e., concomitantly). If desired, either one of the two agents may be administered in low dosage.

In view of this discovery, the aforementioned combinations of drugs can be used in a variety of compositions, methods, and kits, as described herein. Additionally, if desired, structural or functional analogs may be used in place of one or more of the drugs in a combination. Such analogs are described below.

We have also discovered compounds that, alone or in combination, are effective in the treatment, reduction, or prevention of metabolic disorders such as diabetes and obesity. Accordingly, a mammal that has been diagnosed with or is at risk of having a metabolic disorder is administered one, two, three, or more agents from Table 1. Optionally, analogs of these agents may be employed. In the case of diabetes and obesity, for example, such administration may reduce the levels of glucose, reduce levels of LDL-cholesterol, increase the levels of HDL-cholesterol, result in a more favorable ratio between LDL-cholesterol and HDL-cholesterol, reduce the triglyceride values, or reduce serum levels of CRP (C-reactive protein). The ability of the agent to cause the clearance of glucose may be attributed, for example, to its ability to increase insulin production, secretion, or action (e.g., stimulation of glucose uptake by peripheral tissues and/or reduction in hepatic glucose production), reduce the absorption of carbohydrates from the intestines, alter glucose transporter activity (e.g., by increasing GLUT4 expression, intrinsic activity, or translocation), increase the level of insulin-sensitive tissue (e.g., by increasing adipocyte or muscle cell differentiation), or alter gene transcription in adipocytes or muscle cells (e.g., altered secretion of factors from adipocytes and expression of metabolic pathway genes). Optionally, the mammal may also receive other therapeutic regimens.

In one particular example, the mammal being treated is administered two agents listed in Table 1 within 28 days of each other in amounts that together are sufficient to treat, prevent, or reduce the metabolic disorder. The two agents are desirably administered within 14 days of each other, more desirably within seven days of each other, and even more desirably within twenty-four hours of each other, or even simultaneously (i.e., concomitantly). If desired, either one of the two agents may be administered in low dosage.

Diagnosis of Metabolic Disorders

The methods and compositions of the present invention are useful for treating any patient that has been diagnosed with or is at risk of having a metabolic disorder, such as diabetes. A patient in whom the development of a metabolic disorder (e.g., diabetes or obesity) is being prevented may or may not have received such a diagnosis. One in the art will understand that patients of the invention may have been subjected to standard tests or may have been identified, without examination, as one at high risk due to the presence of one or more risk factors.

Diagnosis of metabolic disorders may be performed using any standard method known in the art, such as those described herein. Methods for diagnosing diabetes are described, for example, in U.S. Pat. No. 6,537,806, hereby incorporated by reference. Diabetes may be diagnosed and monitored using, for example, urine tests (urinalysis) that measure glucose and ketone levels (products of the breakdown of fat); tests that measure the levels of glucose in blood; glucose tolerance tests; and assays that detect molecular markers characteristic of a metabolic disorder in a biological sample (e.g., blood, serum, or urine) collected from the mammal (e.g., measurements of Hemoglobin A1c (HbA1c) levels in the case of diabetes).

Patients may be diagnosed as being at risk or as having diabetes if a random plasma glucose test (taken at any time of the day) indicates a value of 200 mg/dL or more, if a fasting plasma glucose test indicates a value of 126 mg/dL or more (after 8 hours), or if an oral glucose tolerance test (OGTT) indicates a plasma glucose value of 200 mg/dL or more in a blood sample taken two hours after a person has consumed a drink containing 75 grams of glucose dissolved in water. The OGTT measures plasma glucose at timed intervals over a 3-hour period. Desirably, the level of plasma glucose in a diabetic patient that has been treated according to the invention ranges between 160 to 60 mg/dL, between 150 to 70 mg/dL, between 140 to 70 mg/dL, between 135 to 80 mg/dL, and preferably between 120 to 80 mg/dL.

Optionally, a hemoglobin A1c (HbA1c) test, which assesses the average blood glucose levels during the previous two and three months, may be employed. A person without diabetes typically has an HbA1c value that ranges between 4% and 6%. For every 1% increase in HbA1c, blood glucose levels increases by approximately 30 mg/dL and the risk of complications increases. Preferably, the HbA1c value of a patient being treated according to the present invention is reduced to less than 9%, less than 7%, less than 6%, and most preferably to around 5%. Thus, the HbA1c levels of the patient being treated are preferably lowered by 10%, 20%, 30%, 40%, 50%, or more relative to such levels prior to treatment.

Gestational diabetes is typically diagnosed based on plasma glucose values measured during the OGTT. Since glucose levels are normally lower during pregnancy, the threshold values for the diagnosis of diabetes in pregnancy are lower than in the same person prior to pregnancy. If a woman has two plasma glucose readings that meet or exceed any of the following numbers, she has gestational diabetes: a fasting plasma glucose level of 95 mg/dL, a 1-hour level of 180 mg/dL, a 2-hour level of 155 mg/dL, or a 3-hour level of 140 mg/dL.

Ketone testing may also be employed to diagnose type 1 diabetes. Because ketones build up in the blood when there is not enough insulin, they eventually accumulate in the urine. High levels of blood ketones may result in a serious condition called ketoacidosis.

The use of any of the above tests or any other tests known in the art may be used to monitor the efficacy of the present treatment. Since the measurements of hemoglobin A1c (HbA1c) levels is an indication of average blood glucose during the previous two to three months, this test may be used to monitor a patient's response to diabetes treatment.

Bezafilbrate

Bezafibrate (2-[4-2-[(4-chlorobenzoyl)amino]-ethyl]phenozy]-2-methylpropanoic acid) has the following structure:

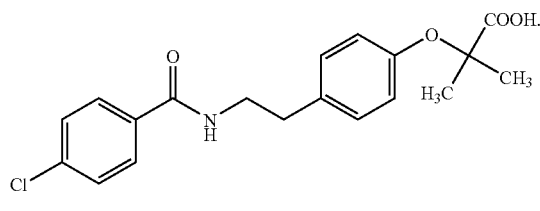

The synthesis of bezafibrate is described in U.S. Pat. No. 3,781,328.

Bezafibrate Analogs

Bezafibrate analogs include binifibrate, ciprofibrate, clinofibrate, clofibrate, etofibrate, fenofibrate, and gemfibrozil. Other bezafibrate analogs are described by formula (I).

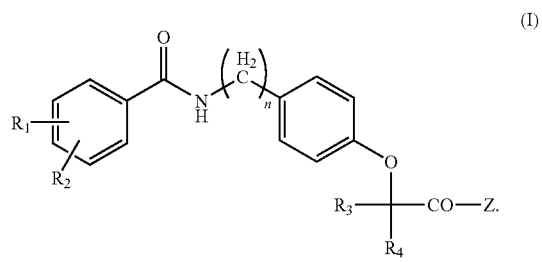

In this formula, each of $R_1$ and $R_2$ is, independently, hydrogen, halogen, $C_{1-4}$ alkyl, and $C_{1-4}$ alkoxy, each of $R_3$ and $R_4$ is, independently, hydrogen and $C_{1-4}$ alkyl, n is 1, 2, and 3, and Z is hydroxyl and $C_{1-4}$ alkyl.

Specific bezafibrate analogs of formula (I) are alpha-[4-(2-methoxy-5-chlorobenzoylaminoethyl)-phenoxy-]isobutyric acid, alpha-[4-(4-methylbenzoylaminomethyl)-phenoxy]-isobutyric acid, alpha-[4-(2-methylbenzoylaminoethyl)-phenoxy]-isobutyric acid, and alpha-[4-(4-chlorobenzoylaminoethyl)-phenoxy]-proprionic acid.

Bezafibrate analogs are also described in U.S. Pat. Nos. 3,262,850; 3,674,836; 3,716,583; 3,723,446; 3,948,973; 4,010,279; 4,026,896; 4,042,711; 4,058,552; 4,151,303; 4,153,728; 4,238,506; 4,318,923; and 4,409,240, each of which is hereby incorporated by reference.

PPAR Agonists

PPARs (Peroxisome Proliferator-Activated receptors) are ligand-activated transcription factors belonging to the nuclear receptor superfamily. Three different PPARs have been identified to date (PPARα, PPARβ and PPARγ) each displaying distinct tissue distribution pattern. PPARs are activated by natural ligands such as fatty acids and eicosanoids (leukotrienes, prostaglandins) and by pharmacological agonists such as fibrates, binding to PPARα and glitazones, binding to PPARγ. Upon ligand activation, PPARs regulate the transcription of several genes. Activated PPARs heterodimerize with another nuclear receptor, the retinoid X receptor, and modify the transcription of target genes after binding to specific peroxisome proliferator response elements (PPRE).

Bezafibrate is a fibrate and thus a PPARα agonist. Because of the interaction between PPARα and PPARγ, PPARγ agonists may nonetheless be used in place of bezafibrate in the compositions, methods, and kits of the invention. For example, glitazones (e.g., balaglitazone, troglitazone, pioglitazone, ciglitazone, englitazone, rosiglitazone, darglitazone, englitazone, netoglitazone, KRP-297, JTT-501, NC-2100, NIP-223, MCC-555, L-764486, and CS-011), also referred to as thiazolidinediones, can be used in combination with cinnamic acid, diflunisal, or an analog thereof, for treating a patient having a metabolic disorder. Similarly, tyrosine-based PPARγ modulators (e.g., GI262570; [(S)-2-(2-benzoylphenylamino)-3-[4-[2-(5-methyl-2-phenyl-2-oxazol-4-yl) ethoxy]phenyl]propionic acid, and GW347845 (Cobb et al., J Med. Chem. 41:5055-5069, 1998)) can also be substituted for bezafibrate, as can other PPARγ agonists (e.g., 3-(2,4-dichlorobenzyl)-2-methyl-N-(pentylsulfonyl)-3H-benzimidazole-5-carboxamide (FK614)).

Other PPAR agonists that may be used in lieu of bezafibrate in the compositions, methods, and kits of the invention are AA-10090, AD-5075, AMG-131, ARH-049020, AVE-0847, AVE-8134, AY-31637, BAY-549801, bexarotene, BM-131246, BM-501050, CLX-0921, CLX-0940, DRF-10945, DRF-4832, E-3030, farglitazar, fenofibrate/metformin, GW-0072, GW-1929, GW-2570, GW-409544, GW-409890, GW-501516, GW-5393, GW-590735, GW-7282, GW-9578, KRP-101, KT-6207, L-764406, LF-200337, LG-101506, LR-90, LY-465608, LY-510929, LY-518674, MBX-102, MK-0767, muraglitazar, naveglitazar, NC-2100, NS-220, ONO-5129, oxeglitazar, PD-72953, R-119702, ragaglitazar, reglitazar, SB-219994, tesaglitazar, 641597, and TY-51501.

Statins

Statins or statin-containing drug combinations may be used in lieu of bezafibrate in the compositions, methods, and kits of the invention. Exemplary statins and statin-containing combinations are acitemate, amlodipine/atorvastatin, atorvastatin, atorvastatin/torcetrapib, BAY102987, BAY X 2678, BB476, bervastatin, BMY21950, BMY22089, cerivastatin, colestolone, CP83101, crilvastatin, dalvastatin, DMP565, ezetimibe/simvastatin, fluvastatin, glenvastatin, L659699, L669262, mevastatin, nicotinic acid/lovastatin, nicotinic acid/simvastatin, P882222, P882284, PD134965, PD135022, pitavastatin, rosuvastatin, RP61969, S2468, SC37111, SC45355, simvastatin, SQ33600, SR12813, SR45023A, U20685, and U88156.

NSAIDs

NSAIDs may also be used in lieu of bezafibrate in the combinations, methods, and kits of the invention. Suitable NSAIDs include A183827, ABT963, aceclofenac, acemetacin, acetyl salicylic acid, AHR10087, alclofenac, alminoprofen, ampiroxicam, amtolmetin guacil, apazone, aspirin, atlipprofen methyl ester, AU8001, benoxaprofen, benzydamine flufenamate, bermoprofen, bezpiperylon, BF388, BF389, BIRL790, BMS347070, bromfenac, bucloxic acid, butibufen, BW755C, C53, C73, C85, carprofen, CBS1108, celecoxib, CHF2003, chlorobiphenyl, choline magnesium trisalicylate, CHX108, cimicoxib, cinnoxicam, clidanac, CLX1205, COX-2 inhibitor (PharmaVU/Vanderbilt University), CP331, CS502, CS706, D1367, darbufelone, deracoxib, dexibuprofen, dexibuprofen lysine, dexketoprofen, DFP, DFU, diclofenac (e.g., diclofenac potassium, diclofenac sodium), diflunisal, DP155, DRF4367, E5110, E6087, eltenac, ER34122, esflurbiprofen, etoricoxib, F025, felbinac ethyl, fenbufen, fenclofenac, fenclozic acid, fenclozine, fenoprofen, fentiazac, feprazone, filenadol, flobufen, florifenine, flosulide, flubichin methanesulfonate, flufenamic acid, fluprofen, flurbiprofen, FPL62064, FR122047, FR123826, FR140423, FR188582, FS205397, furofenac, GR253035, GW406381, HAI105, HAI106, HCT2035, HCT6015, HGP12, HN3392, HP977, HX0835. HYAL AT2101, ibufenac, ibuprofen, ibuproxam-beta-cyclodextrin, icodulinum, IDEA070, iguratimod, imrecoxib, indomethacin, indoprofen, IP751, isoxepac, isoxicam, KC764, ketoprofen, L652343, L745337, L748731, L752860, L761066, L768277, L776967, L783003, L784520, L791456, L804600, L818571, LAS33815, LAS34475, licofelone, LM 4108, lobuprofen, lornoxicam, lumiracoxib, mabuprofen, meclofenamic acid, meclofenamate sodium, mefenamic acid, meloxicam, mercaptoethylguanidine, mesoporphyrin, metoxibutropate, miroprofen, mofebutazone, mofezolac, MX1094, nabumetone, naproxen sodium, naproxen-sodium/metoclopramide, NCX1101, NCX284, NCX285, NCX4016, NCX4215, NCX530, niflumic acid, nitric oxide-based COX-2 inhibitors and NSAIDs (NitroMed), nitrofenac, nitroflurbiprofen, nitronaproxen, NS398, ocimum sanctum oil, ONO3144, orpanoxin, oxaprozin, oxindanac, oxpinac, oxycodone/ibuprofen, oxyphenbutazone, P10294, P54, P8892, pamicogrel, parcetasal, parecoxib, PD138387, PD145246, PD164387, pelubiprofen, pemedolac, phenylbutazone, pirazolac, piroxicam, piroxicam beta-cyclodextrin, piroxicam pivalate, pirprofen, pranoprofen, resveratrol, R-ketoprofen, R-ketorolac, rofecoxib, RP66364, RU43526, RU54808, RWJ63556, S19812, S2474, S33516, salicylsalicylic acid, satigrel, SC236, SC57666, SC58125, SC58451, SFPP, SKF105809, SKF86002, sodium salicylate, sudoxicam, sulfasalazine, sulindac, suprofen, SVT2016, T3788, TA60, talmetacin, talniflumate, tazofelone, tebufelone, tenidap, tenoxican, tepoxalin, tiaprofenic acid, tilmacoxib, tilnoprofen arbamel, tinoridine, tiopinac, tioxaprofen, tolfenamic acid, tolmetin, triflusal, tropesin, TY10222, TY10246, TY10474, UR8962, ursolic acid, valdecoxib, WAY120739, WY28342, WY41770, ximoprofen, YS134, zaltoprofen, zidometacin, and zomepirac.

Cinnamic Acid and Analogs Thereof

Cinnamic acid (3-phenyl-2-propenoic acid) has the structure $C_6H_5CH=CHCOOH$. Cinnamic acid analogs are described by formula (II):

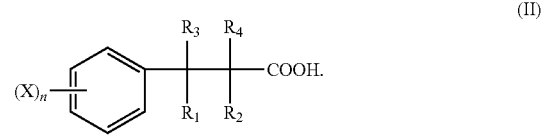

In formula (II), $R_1$ and $R_2$ each represent a hydrogen atom or a $C_{1-4}$ alkyl group; $R_3$ and $R_4$ each represent a hydrogen atom or may be combined together to form an additional chemical bond; X represents a hydroxyl group, a halogen atom, a straight or branched chain saturated or unsaturated $C_{1-4}$ alkyl group, a straight or branched chain saturated or unsaturated $C_{1-4}$ alkoxy group, a $C_{1-4}$ acyloxy group, or a $C_{3-6}$ cycloalkyl group; n is zero or an integer from 1 to 3, with the proviso that when n is 2 or 3, each X may be the same or different and that when two X's are commonly the alkyl or alkoxy group, both X's may be combined together to form a ring.

Specific cinnamic acid analogs of formula (II) are hydrocinnamic acid, 2-, 3- and 4-methylhydrocinnamic acid, 2-, 3- and 4-ethylhydrocinnamic acid, 2-, 3- and 4-propylhydrocinnamic acid, 2-, 3- and 4-hydroxyhydrocinnamic acid, 2-, 3- and 4-methoxyhydrocinnamic acid, 2-, 3- and 4-ethoxyhydrocinnamic acid, 2-, 3- and 4-chlorohydrocinnamic acid, 2-, 3- and 4-bromohydrocinnamic acid, 2-, 3- and 4-fluorohydrocinnamic acid, 2,4-, 2,5- and 3,4-dimethylhydrocinnamic acid, 2,4-diethylhydrocinnamic acid, 2,3-, 2,4-, 2,5-, 2,6-, 3,4- and 3,5-dihydroxyhydrocimmamic acid, 2,3-, 2,4-, 2,5-, 2,6-, 3,4- and 3,5-dimethoxyhydrocinnamic acid, 2,3-, 2,4-, 2,5-, 2,6-, 3,4- and 3,5-diethoxyhydrocinnamic acid, 2,3-, 2,4- and 3,4-dipropoxyhydrocinnamic acid, 2-hydroxy-3-methoxyhydrocinnamic acid, 3-hydroxy-4-methoxyhydrocinnamic acid, 4-hydroxy-3-methoxyhydrocinnamic acid, 3-ethoxy-4-methoxyhydrocinnamic acid, 4-hydroxy-3-methoxyhydrocinnamic acid, 2-ethoxy-3-methoxyhydrocinnamic acid, 3-ethoxy-4-methoxyhydrocinnamic acid, 4-ethoxy-3-methoxyhydrocinnamic acid, 3-methoxy-2-propoxyhydrocinnamic acid, 3-methoxy-4-propoxyhydrocinnamic acid, 3,4-methylenedioxyhydrocinnamic acid, 2,4-, 2,6- and 3,4-dichlorohydrocinnamic acid, 2,3,4-, 2,4,5- and 3,4,5-trimethoxyhydrocinnamic acid, 2-bromo-4-hydroxy-5-methoxyhydrocinnamic acid, 4-isopropylhydrocinnamic acid, 3- and 4-isopropoxyhydrocinnamic acid, 3- and 4-isobutoxyhydrocinnamic acid, 3- and 4-sec-butoxyhydrocinnamic acid, 3-methoxy-4-isopropoxyhydrocinnamic acid, 2-, 3- and 4-allyloxyhydrocinnamic acid, 2-, 3- and 4-methallyloxyhydrocinnamic acid, 3-methoxy-4-allyloxyhydrocinnamic acid, 3-methoxy-4-methallyloxyhydrocinnamic acid, 2-, 3- and 4-acetoxyhydrocinnamic acid, 3,4-trimethylenehydrocinnamic acid, and α- and/or β-alkyl-substituted hydrocinnamic acids carrying substituents the same as those mentioned in the case of the above-mentioned hydrocinnamic acids; and aromatic unsaturated carboxylic acids such as 2-, 3- and 4-methylcinnamic acid, 2-, 3- and 4-ethylcinnamic acid, 2-, 3- and 4-propylcinnamic acid, 2-, 3- and 4-hydroxycinnamic acid, 2-, 3- and 4-methoxycinnamic acid, 2-, 3- and 4-ethoxycinnamic acid, 2-, 3- and 4-propoxycinnamic acid, 2-, 3- and 4-butoxycinnamic acid, 2-, 3- and 4-fluorocinnamic acid, 2-, 3- and 4-chlorocinnamic acid, 2-, 3- and 4-bromocinnamic acid, 2,4- and 2,5 and 3,4-dimethylcinnamic acid, 2,4-diethylcinnamic acid, 2,3-, 2,4-, 2,5-2,6-, 3,4- and 3,5-dihydroxycinnamic acid, 2,3-, 2,4-, 2,5-, 2,6-, 3,4- and 3,5-dimethoxycinnamic acid, 2,3-, 2,4-, 2,5-, 2,6-, 3,4- and 3,5-diethoxycinnamic acid, 2,3-, 2,4- and 3,4-dipropoxycinnamic acid, 2-hydroxy-3-methoxycinnamic acid, 3-hydroxy-4-methoxycinnamic acid, 4-hydroxy-3-methoxycinnamic acid, 2-ethoxy-3-methoxycinnamic acid, 3-ethoxy-4-methoxycinnamic acid, 4-ethoxy-3-methoxycinnamic acid, 3-methoxy-2-propoxycinnamic acid, 3-methoxy-4-propoxycinnamic acid, 3,4-methylenedioxycinnamic acid, 2,3,4-, 2,4,5- and 3,4,5-trimethoxycinnamic acid, 2-bromo-4-hydroxy-5-methoxycinnamic acid, 4-isopropylcinnamic acid, 3- and 4-isopropoxycinnamic acid, 3- and 4-isobutoxycinnamic acid, 3- and 4-sec-butoxycinnamic acid, 3-methoxy-4-isoproxycinnamic acid, 2-, 3- and 4-allyloxycinnamic acid, 2-, 3- and 4-methallyloxycinnamic acid, 3-methoxy-4-allyloxycinnamic acid, 3-methoxy-4-methallyloxycinnamic acid, 2-, 3- and 4-acetoxycinnamic acid, 3,4-trimethylenecinnamic acid, and α- and/or β-alkylsubstituted cinnamic acids carrying substituents the same as those mentioned in the case of the above-mentioned cinnamic acids.

Diflunisal

Diflunisal (2',4'-difluoro-4-hydroxy-[1,1'-biphenyl]-3-carboxylic acid) is an NSAID having the structure:

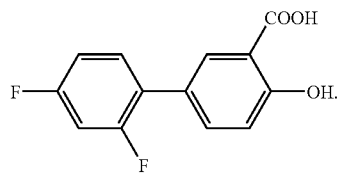

Methods of making diflunisal are described in U.S. Pat. No. 3,714,226.

Diflunisal Analogs

Diflunisal analogs are described by formula (III):

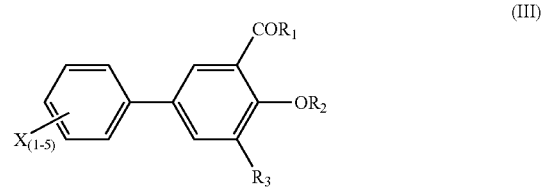

wherein each X is, independently, a halogen atom; $R_1$ is selected from the group consisting of hydroxy, phenoxy, di($C_1$-$C_4$)alkylamino, di($C_1$-$C_4$)alkylamino ($C_1$-$C_4$)alkoxy; $R_2$ is selected from the group consisting of hydrogen and ($C_1$-$C_4$)alkanoyl (such as acetyl, propionyl and butyryl); and $R_3$ is selected from the group consisting of hydrogen and methyl.

Other diflunisal analogs are flufenisal, 2-hydroxy-5-(4'-fluorophenyl)benzoic acid; 2-acetoxy-5-(4'-fluorophenyl)benzoic acid; 2-hydroxy-5-(2'-fluorophenyl)benzoic acid; 2-hydroxy-5-(3'-fluorophenyl)benzoic acid; 2-hydroxy-5-pentafluorophenyl benzoic acid; 2-hydroxy-3-methyl-5-(4'-fluorophenyl)benzoic acid; 2-hydroxy-5-(4'-chlorophenyl)benzoic acid; N,N-dimethyl-5-(4'-fluorophenyl)salicylamide; β-diethylaminoethyl-5-(4'-fluorophenyl)salicylate; phenyl-5-(4'-fluorophenyl)salicylate; aluminum-2-acetoxy-5-(4'-fluorophenyl)-benzoate salt; aluminum-2-hydroxy-5-(4'-fluorophenyl)-benzoate salt; choline-2-acetoxy-5-(4'-fluorophenyl)-benzoate salt; choline-2-hydroxy-5-(4'-fluorophenyl)-benzoate salt; sodium-2-acetoxy-5-(4'-fluorophenyl)-benzoate salt; sodium-2-hydroxy-5-(4'-fluorophenyl)-benzoate salt; 2-hydroxy-5-(pentafluorophenyl)-benzoic acid; 2-acetoxy-5-(pentafluorophenyl)-benzoic acid; β-diethylaminoethyl-2-hydroxy-5-(4'-fluorophenyl)-benzoate; β-diethylaminoethyl-2-acetoxy-5-(4'-fluorophenyl)-benzoate; 2-hydroxy-5-(4'-fluorophenyl)-benzamide; 2-hydroxy-5-(4'-fluorophenyl)-3-methyl benzamide; 2-acetoxy-5-(4'-fluorophenyl)-benzamide; 2-acetoxy-5-(4'-fluorophenyl)-benzmorpholide; 2-hydroxy-5-(4'-fluoro-2'-methoxyphenyl)benzoic acid; 2-acetoxy-5-(4'-fluoro-2'-methoxyphenyl)benzoic acid; 2-hydroxy-5-(4'-fluoro-2'-methylphenyl)benzoic acid; 2-acetoxy-5-(4'-fluoro-3'-methylphenyl)benzoic acid; 2-hydroxy-3-allyl-5-(4'-fluorophenyl)benzoic acid; 2-hydroxy-3-propyl-5-(4'-fluorophenyl)benzoic acid; and the compounds described in U.S. Pat. Nos. 3,674,870, 3,681,445, 3,692,821, 3,714,226, 4,044,049, 4,542,158, and 6,593,365.

If desired, other NSAIDs can be used in place diflunisal. Suitable NSAIDs include A183827, ABT963, aceclofenac, acemetacin, acetyl salicylic acid, AHR10037, alclofenac, alminoprofen, ampiroxicam, amtolmetin guacil, apazone, aspirin, atliprofen methyl ester, AU8001, benoxaprofen, benzydamine flufenamate, bermoprofen, bezpiperylon, BF388, BF389, BIRL790, BMS347070, bromfenac, bucloxic acid, butibufen, BW755C, C53, C73, C85, carprofen, CBS1108, celecoxib, CHF2003, chlorobiphenyl, choline magnesium trisalicylate, CHX108, cimicoxib, cinnoxicam, clidanac, CLX1205, COX-2 inhibitor (PharmaVU/Vanderbilt University), CP331, CS502, CS706, D1367, darbufelone, deracoxib, dexibuprofen, dexibuprofen lysine, dexketoprofen, DFP, DFU, diclofenac (e.g., diclofenac potassium, diclofenac sodium), diflunisal, DP155, DRF4367, E5110, E6087, eltenac, ER34122, esflurbiprofen, etoricoxib, F025, felbinac ethyl, fenbufen, fenclofenac, fenclozic acid, fenclozine, fenoprofen, fentiazac, feprazone, filenadol, flobufen, florifenine, flosulide, flubichin methanesulfonate, flufenamic acid, fluprofen, flurbiprofen, FPL62064, FR122047, FR123826, FR140423, FR188582, FS205397, furofenac, GR253035, GW406381, HAI105, HAI106, HCT2035, HCT6015, HGP12, HN3392, HP977, HX0835. HYAL AT2101, ibufenac, ibuprofen, ibuproxam-beta-cyclodextrin, icodulinum, IDEA070, iguratimod, imrecoxib, indomethacin, indoprofen, IP751, isoxepac, isoxicam, KC764, ketoprofen, L652343, L745337, L748731, L752860, L761066, L768277, L776967, L783003, L784520, L791456, L804600, L818571, LAS33815, LAS34475, licofelone, LM 4108, lobuprofen, lornoxicam, lumiracoxib, mabuprofen, meclofenamic acid, meclofenamate sodium, mefenamic acid, meloxicam, mercaptoethylguanidine, mesoporphyrin, metoxibutropate, miroprofen, mofebutazone, mofezolac, MX1094, nabumetone, naproxen sodium, naproxen-sodium/metoclopramide, NCX1101, NCX284, NCX285, NCX4016, NCX4215, NCX530, niflumic acid, nitric oxide-based COX-2 inhibitors and NSAIDs (NitroMed), nitrofenac, nitroflurbiprofen, nitronaproxen, NS398, ocimum sanctum oil, ONO3144, orpanoxin, oxaprozin, oxindanac, oxpinac, oxycodone/ibuprofen, oxyphenbutazone, P10294, P54, P8892, pamicogrel, parcetasal, parecoxib, PD138387, PD145246, PD164387, pelubiprofen, pemedolac, phenylbutazone, pirazolac, piroxicam, piroxicam beta-cyclodextrin, piroxicam pivalate, pirprofen, pranoprofen, resveratrol, R-ketoprofen, R-ketorolac, rofecoxib, RP66364, RU43526, RU54808, RWJ63556, S19812, S2474, S33516, salicylsalicylic acid, satigrel, SC236, SC57666, SC58125, SC58451, SFPP, SKF105809, SKF86002, sodium salicylate, sudoxicam, sulfasalazine, sulindac, suprofen, SVT2016, T3788, TA60, talmetacin, talniflumate, tazofelone, tebufelone, tenidap, tenoxican, tepoxalin, tiaprofenic acid, tilmacoxib, tilnoprofen arbamel, tinoridine, tiopinac, tioxaprofen, tolfenamic acid, tolmetin, triflusal, tropesin, TY10222, TY10246, TY10474, UR8962, ursolic acid, valdecoxib, WAY120739, WY28342, WY41770, ximoprofen, YS134, zaltoprofen, zidometacin, and zomepirac.

Additional Therapeutic Agents

The present invention involves the administration of an effective amount of one, two, three, four, or more agents listed in Table 1 to a mammal at risk of having or having a metabolic disorder, thereby treating, preventing, and reducing such a disorder.

In the case of diabetes, the agent of the invention increases the clearance of glucose from the plasma by any mechanism thereby reducing glucose levels to normoglycemic levels. For example, a combination of the invention may alter the insulin signaling pathway, reduce the absorption of carbohydrates from the intestines, alter glucose transporter activity (e.g., by increasing GLUT4 expression, intrinsic activity, or translocation), increase the level of insulin-sensitive tissue (e.g., by increasing adipocyte or muscle cell differentiation), or alter gene transcription in adipocytes or muscle cells (e.g., altered secretion of factors from adipocytes expression of metabolic pathway genes). Given that plasma glucose levels prior to eating typically range between 80 and 120 mg/dL and that postprandial blood levels range between 100 to 140 mg/dL, the plasma glucose levels of the patient being treated according to the invention is stabilized such that glucose levels range between 60 and 150 mg/dL, between 70 and 140 mg/dL, between 80 and 130 mg/dL, and preferably between 80 and 120 mg/dL prior to a meal and between 90 mg/dL to 160 mg/dL, between 90 mg/dL to 150 mg/dL, and preferably between 90 to 140 mg/dL two hours after eating. A particularly desirable result of treatment is a reduction of any of the symptoms associated with the metabolic disorder.

Analogs of any of the compounds listed in Table 1 may be used in any of the methods, kits, and compositions of the invention. Analogs are known in the art (e.g., as described herein). Acemetacin analogs are described in German patent DE 2234651 and U.S. Pat. No. 3,910,952. Acenocoumarol analogs are described in U.S. Pat. No. 2,648,682. Acetaminophen analogs are described in U.S. Pat. No. 2,998,450 and German patent DE 453577. Acetazolamide analogs are described in U.S. Pat. No. 2,554,816. Acetohexamide analogs are described in GB 912789. Acetyldigitoxin analogs are described in U.S. Pat. No. 2,776,963. Alachlor analogs are described in NL 6602564. Albuterol (Salbutamol) analogs are described in ZA 67 05591 and U.S. Pat. No. 3,644,353. Alprenolol analogs are described in NL 6605692 and NL 6612958. Ametryn analogs are described in CH 337019 and U.S. Pat. No. 3,558,622. Atrazine analogs are described in CH 342784, CH 342785, HU 149189, and FR 1317812. Azathioprine analogs are described in U.S. Pat. No. 3,056,785 and benzbromarone analogs are described in BE 553621 and U.S. Pat. No. 3,012,042. Bezafibrate analogs are described in DE 2149070 and U.S. Pat. No. 3,781,328. Bopindolol analogs are described in U.S. Pat. No. 4,340,541 and DE 2635209. Brimonidine analogs are described in U.S. Pat. No. 3,890,319 and German patent DE 2309160. Brompheniramine (e.g., maleate salt) analogs are described in U.S. Pat. No. 2,567,245, U.S. Pat. No. 2,676,964, and U.S. Pat. No. 3,061,517. Candesartan (e.g., cilexetil salt) analogs are described in EP 459136 and U.S. Pat. No. 5,196,444, captopril analogs are described in DE 2703828, U.S. Pat. No. 4,046,889, and U.S. Pat. No. 4,105,776, and carbamazepine analogs are described in U.S. Pat. No. 2,948,718. Carbinoxamine (e.g., maleate salt) analogs are described in U.S. Pat. No. 2,606,195, U.S. Pat. No. 2,800,485, and GB 905993. Carisoprodol analogs are described in U.S. Pat. No. 2,937,119 and cefamandole (e.g., nafate salt) analogs are described in German patents DE 2018600 and DE 2312997, as well as U.S. Pat. No. 3,641,021 and U.S. Pat. No. 3,840,531. Cefpodoxime Proxetil analogs are described in EP 49118 and U.S. Pat. No. 4,486,425. Ciclopirox analogs are described in ZA 69 06039 and U.S. Pat. No. 3,883,545. Clenbuterol analogs are described in ZA 67 05692 and U.S. Pat. No. 3,536,712. Diacerein analogs are described in German patent DE 2711493, Japanese Patent JP Kokai 83 225015, U.S. Pat. No. 4,244,968, and U.S. Pat. No. 4,346,103. Diclofenac (e.g., sodium salt) analogs are described in U.S. Pat. No. 3,558,690 and NL 6604752. Dicloxacillin (e.g., sodium salt) analogs are described in GB 978299 and U.S. Pat. No. 3,239,507. Diflunisal analogs are described in ZA 67 01021, FR 1522570, and U.S. Pat. No. 3,714,226. Dimenhydrinate analogs are described in U.S. Pat. No. 2,499,058 and U.S. Pat. No. 2,534,813. Diphemanil Methylsulfate analogs are described in U.S. Pat. No. 2,739,968. Diphenhydramine (e.g., hydrochloride salt) analogs are described in U.S. Pat. No. 2,421,714, U.S. Pat. No. 2,427,878, and U.S. Pat. No. 2,397,799 as well as Japanese patent JP 64 243. Diphenidol (e.g., hydrochloride salt) analogs are described in U.S. Pat. No. 2,411,664 and GB 683950. Dipivefrin (e.g., hydrochloride salt) analogs are described in German patents DE 2152058 and DE 2343657 as well as U.S. Pat. No. 4,085,270, U.S. Pat. No. 3,809,714, and U.S. Pat. No. 3,839,584. Dirithromycin analogs are described in BE 840431 and U.S. Pat. No. 4,048,306. 5-Hydroxytryptophan (e.g., DL form) analogs are described in CA 619472 and GB 845034. Doxapram (e.g., hydrochloride salt) analogs are described in BE 613734 and U.S. Pat. No. 3,192,206. Doxycycline analogs are described in U.S. Pat. No. 3,019,260 and U.S. Pat. No. 3,200,149. Enalaprilat analogs are described in EP 12401 and U.S. Pat. No. 4,374,829. Ethopropazine (e.g., hydrochloride salt) analogs are described in U.S. Pat. No. 2,607,773. Etoposide analogs are described in U.S. Pat. No. 3,524,844. Evans Blue analogs are described in German patents DE 35341, DE 38802, DE 3949, DE 57327, and DE 75469. Exemestane analogs are described in U.S. Pat. No. 4,808,616 and German patent DE 3622841. Flunixin (e.g., meglumine salt) analogs are described in BE 679271, BE 812772, as well as U.S. Pat. No. 3,337,570 and U.S. Pat. No. 3,839,344. Gemfibrozil analogs are described in DE 1925423 and U.S. Pat. No. 3,674,836 and U.S. Pat. No. 4,126,637. Indocyanine Green analogs are described in U.S. Pat. No. 2,895,955. Indomethacin analogs are described in U.S. Pat. No. 3,161,654 and BE 679678. Iopanoic Acid analogs are described in U.S. Pat. No. 2,705,726. Iophenoxic Acid analogs are described in GB 726987. Iopromide analogs are described in DE 2909439 and U.S. Pat. No. 4,364,921. Isoproterenol (e.g., sulfate salt) analogs are described in German patent DE 723278 and U.S. Pat. Nos. 2,308,232 and 2,715,141. Isotretinoin analogs are described in EP 111325 and U.S. Pat. No. 4,556,518. Ketoconazole analogs are described in German patent DE 2804096, U.S. Pat. No. 4,144,346, and U.S. Pat. No. 4,223,036. Ketotifen (e.g., fumarate salt) analogs are described in German patent DE 2111071 and U.S. Pat. No. 3,682,930. Lamivudine analogs are described in PCT WO 91/17159. Leflunomide analogs are described in German patent DE 2854439 and U.S. Pat. No. 4,284,786. Levocabastine (e.g., hydrochloride salt) analogs are described in EP 34415 and U.S. Pat. No. 4,369,184. Loxapine (e.g., hydrochloride salt) analogs are described in NL 6406089 and U.S. Pat. No. 3,546,226 and U.S. Pat. No. 3,412,193. Mebhydroline (e.g., 1,5-Naphthalenedisulfonate salt) analogs are described in U.S. Pat. No. 2,786,059. Meclofenoxate analogs are described in FR M398. Mefenamic Acid analogs are described in BE 605302 and U.S. Pat. No. 3,138,636. Meloxicam analogs are described in U.S. Pat. No. 4,233,299. Melphalan analogs are described in U.S. Pat. No. 3,032,584 and U.S. Pat. No. 3,032,585. Mercaptoethanol analogs are described in U.S. Pat. No. 2,402,665 and U.S. Pat. No. 3,394,192. Metaproterenol (e.g., hemisulfate salt) analogs are described in U.S. Pat. No. 3,341,594 and BE 611502. Methacholine analogs are described in U.S. Pat. No. 2,040,146. Methdilazine analogs are described in U.S. Pat. No. 2,945,855. Methylergonovine (e.g., maleate salt) analogs are described in U.S. Pat. No. 2,265,207. Nateglinide analogs are described in EP 196222 and U.S. Pat. No. 4,816,484. Nefopam analogs are described in NL 6606390 and U.S. Pat. No. 3,830,803. Nimesulide analogs are described in BE 801812 and U.S. Pat. No. 3,840,597. Norepinephrine (e.g., bitartrate salt) analogs are described in U.S. Pat. No. 2,774,789. Olanzapine analogs are described in EP 454436 and U.S. Pat. No. 5,229,382. Oleandomycin analogs are described in U.S. Pat. No. 2,757,123 and U.S. Pat. No. 2,842,481. Orphenadrine (e.g., citrate salt) analogs are described in U.S. Pat. No. 2,567,351 and U.S. Pat. No. 2,991,225. Oxaprozin analogs are described in FR 2001036, GB 1206403, and U.S. Pat. No. 3,578,671. Oxybutynin (e.g., chloride salt) analogs are described in GB 940540. Oxymetazoline (e.g., hydrochloride salt) analogs are described in German patent DE 1117588. Pergolide (e.g., mesylate salt) analogs are described in U.S. Pat. No. 4,166,182. Phenacemide analogs are described in U.S. Pat. No. 2,887,513. Phensuximide analogs are described in U.S. Pat. No. 2,643,258. Phenylbutazone analogs are described in U.S. Pat. No. 2,562,830 and GB 812449. Phenylephrine analogs are described in U.S. Pat. No. 1,932,347 and U.S. Pat. No. 1,954,389. Phenyloin analogs are described in U.S. Pat. No. 2,409,754. Prazosin (e.g., hydrochloride salt) analogs are described in GB 1156973, U.S. Pat. No. 3,511,836, and NL 7206067. Promethazine (e.g., hydrochloride salt) analogs are described in U.S. Pat. No. 2,530,451 and U.S. Pat. No. 2,607,773. Prostaglandin (e.g., Prostaglandin E) analogs are described in GB 851827, U.S. Pat. No. 3,598,858, NL 6505799, DE 2126127, U.S. Pat. No. 3,657,327, U.S. Pat. No. 3,069,322, and U.S. Pat. No. 3,598,858. Pyrilamine (e.g., maleate salt) analogs, are described in U.S. Pat. No. 2,502,151. Quinacrine analogs are described in German patents DE 553072, DE 571499, U.S. Pat. No. 2,113,357, U.S. Pat. No. 1,782,727, and U.S. Pat. No. 1,889,704. Ritodrine (e.g., hydrochloride salt) analogs are described in BE 660244 and U.S. Pat. No. 3,410,944. Rolipram analogs are described in BE 826923 and U.S. Pat. No. 4,193,926. Succinylcholine analogs are described in AT 171411. Sulfaguanidine analogs are described in U.S. Pat. No. 2,218,490, U.S. Pat. No. 2,229,784, U.S. Pat. No. 2,233,569, and GB 551524. Sulfamethizole analogs are described in U.S. Pat. No. 2,447,702. Suprofen analogs are described in U.S. Pat. No. 4,035,376. Telmisartan analogs are described in EP 502314. Terbutaline (e.g., sulfate salt) analogs are described in BE 704932 and U.S. Pat. No. 3,937,838. Tetrahydrozoline (e.g., hydrochloride salt) analogs are described in U.S. Pat. No. 2,731,471 and U.S. Pat. No. 2,842,478. Timidazole analogs are described in U.S. Pat. No. 3,376,311. Tioconazole analogs are described in BE 841309 and U.S. Pat. No. 4,062,966. Tolazoline (e.g., hydrochloride salt) analogs are described in U.S. Pat. No. 2,161,938. Tolfenamic acid analogs are described in NL 6600251 and U.S. Pat. No. 3,313,848. Triamterene analogs are described in U.S. Pat. No. 3,081,230. Triflupromazine (e.g., hydrochloride salt) analogs are described in GB 813861. Tulobuterol (e.g., hydrochloride salt) analogs are described in German patent DE 2244737. Vincamine analogs are described in German patent DE 2115718 and U.S. Pat. No. 3,770,724. Warfarin analogs are described in U.S. Pat. No. 2,427,578, U.S. Pat. No. 2,765,321, U.S. Pat. No. 2,777,859, and U.S. Pat. No. 3,239,529. Xylazine (e.g., hydrochloride salt) analogs are described in BE 634552, DE 1173475, and U.S. Pat. No. 3,235,550. All of these references are hereby incorporated by reference.

If desired, the patient may also receive additional therapeutic regimens. For example, therapeutic agents may be administered with the agent or agents described herein at concentrations known to be effective for such therapeutic agents. Particularly useful agents include those that reduce glucose levels or those used to treat, prevent, or reduce metabolic disorders. Such agents include those that alter the insulin signaling pathway, such as agents that increase the insulin supply, reduce insulin resistance, increase the effectiveness of insulin, reduce hepatic glucose output, control blood glucose and triglyceride levels, and reduce the absorption of carbohydrates from the intestine. Exemplary agents are sulfonylureas (e.g., acetohexamide, chlorpropamide, tolazamide, tolbutamide, glimepiride, glipizide, and glyburide), non-sulfonylurea secretagogues (e.g., nateglinide and repaglinide), insulin, insulin analogs (e.g., insulin lispro, insulin aspart, insulin glarginine, NPH, lente insulin, ultralente insulin, humulin, novolin), glucagon-like peptides (e.g., GLP-1), exendin-4 (e.g., AAC2993), beta-3 adrenergic receptor agonists (e.g., YM178), PPAR gamma agonists (e.g., FK614), dipeptidyl peptidase IV inhibitors, biguanides (e.g., metformin and metformin/glyburide), thiazalidinediones (e.g., troglitazone, pioglitazone and rosiglitazone), alpha-glucosidase inhibitors (e.g., acarbose and miglitol), immunosuppressants or immunomodulators (e.g., glucocorticoids, cyclophosphamide, cyclosporine A, rapamycin, FK506 cytokines such as IL-4 and -IL-10, OK-432, LZ-8, BCG, and CFA, angiotensin converting enzyme (ACE) inhibitors (e.g., benazepril, captopril, cilazapril, enalapril, enalaprilat, fosinopril, lisinopril, moexipril, perindopril, quinapril, ramipril, and trandolapril), angiotensin II receptor blockers (e.g., candesartan, eprosartan, irbesarten, losartin, telmisartan, and valsartan), antioxidants (e.g., nicotinamide, vitamin E, probucol, MDL29311 and U78518F), and combinations thereof.

It may also be desirable to administer to the patient therapeutic compounds, such as corticosteroids, NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, and tolmetin), COX-2 inhibitors (e.g., rofecoxib, celecoxib, valdecoxib, and lumiracoxib), DMARD, anti-cytokine agents or agents that modulate the immune response to positively effect disease, such as agents that influence cell adhesion, or biologics (i.e., agents that block the action of IL-6, IL-1, IL-2, IL-12, IL-15 or TNFα (e.g., etanercept, adelimumab, infliximab, or CDP-870).

If more than one agent is employed, therapeutic agents may be delivered separately or may be admixed into a single formulation. When agents are present in different pharmaceutical compositions, different routes of administration may be employed. Routes of administration for the various embodiments include, but are not limited to, topical, transdermal, and systemic administration (such as, intravenous, intramuscular, subcutaneous, inhalation, rectal, buccal, vaginal, intraperitoneal, intraarticular, ophthalmic or oral administration). As used herein, "systemic administration" refers to all nondermal routes of administration, and specifically excludes topical and transdermal routes of administration. Desirably, the agent of the invention and additional therapeutic agents are administered within at least 1, 2, 4, 6, 10, 12, 18, 24 hours, 3 days, 7 days, or 14 days apart. The dosage and frequency of administration of each component of the combination can be controlled independently. For example, one compound may be administered three times per day, while the second compound may be administered once per day. Combination therapy may be given in on-and-off cycles that include rest periods so that the patient's body has a chance to recover from any as yet unforeseen side effects. The compounds may also be formulated together such that one administration delivers both compounds. Optionally, any of the agents of the combination may be administered in a low dosage or in a high dosage, each of which is defined herein.

The therapeutic agents of the invention may be admixed with additional active or inert ingredients, e.g., in conventional pharmaceutically acceptable carriers. A pharmaceutical carrier can be any compatible, non-toxic substance suitable for the administration of the compositions of the present invention to a mammal. Pharmaceutically acceptable carriers include, for example, water, saline, buffers and other compounds described for example in the Merck Index, Merck & Co., Rahway, N.J. Slow release formulation or a slow release apparatus may be also be used for continuous administration.

In addition to the administration of therapeutic agents, the second therapeutic regimen may involve transplantation of insulin-producing cells, tissues, or organs (e.g., pancreatic cells, beta pancreatic cells, or pancreas) or a modification to the lifestyle of the patient being treated. Such lifestyle changes may be helpful to control glucose levels and include weight loss, physical exercise, diet control, reduction in alcohol intake, or reduction in smoking.

Corticosteroids

A corticosteroid may be formulated in the composition of the invention or administered to the mammal being treated according to the invention. Suitable corticosteroids include 11-alpha, 17-alpha, 21-trihydroxypregn-4-ene-3,20-dione; 11-beta, 16-alpha, 17,21-tetrahydroxypregn-4-ene-3,20-dione; 11-beta, 16-alpha, 17,21-tetrahydroxypregn-1,4-diene-3,20-dione; 11-beta, 17-alpha, 21-trihydroxy-6-alpha-methylpregn-4-ene-3,20-dione; 11-dehydrocorticosterone; 11-deoxycortisol; 11-hydroxy-1,4-androstadiene-3,17-dione; 11-ketotestosterone; 14-hydroxyandrost-4-ene-3,6,17-trione; 15,17-dihydroxyprogesterone; 16-methylhydrocortisone; 17,21-dihydroxy-16-alpha-methylpregna-1,4,9(11)-triene-3,20-dione; 17-alpha-hydroxypregn-4-ene-3,20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-deoxyaldosterone; 21-deoxycortisone; 2-deoxyecdysone; 2-methylcortisone; 3-dehydroecdysone; 4-pregnene-17-alpha, 20-beta, 21-triol-3,11-dione; 6,17,20-trihydroxypregn-4-ene-3-one; 6-alpha-hydroxycortisol; 6-alpha-fluoroprednisolone, 6-alpha-methylprednisolone, 6-alpha-methylprednisolone 21-acetate, 6-alpha-methylprednisolone 21-hemisuccinate sodium salt, 6-beta-hydroxycortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclometasone dipropionate; aldosterone; algestone; alphaderm; amadinone; amcinonide; anagestone; androstenedione; anecortave acetate; beclomethasone; beclomethasone dipropionate; beclomethasone dipropionate monohydrate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; clobetasol; clobetasol propionate; clobetasone; clocortolone; clocortolone pivalate; clogestone; cloprednol; corticosterone; cortisol; cortisol acetate; cortisol butyrate; cortisol cypionate; cortisol octanoate; cortisol sodium phosphate; cortisol sodium succinate; cortisol valerate; cortisone; cortisone acetate; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; dihydroelatericin a; domoprednate; doxibetasol; ecdysone; ecdysterone; endrysone; enoxolone; flucinolone; fludrocortisone; fludrocortisone acetate; flugestone; flumethasone; flumethasone pivalate; flumoxonide; flunisolide; fluocinolone; fluocinolone acetonide; fluocinonide; 9-fluorocortisone; fluocortolone; fluorohydroxyandrostenedione; fluorometholone; fluorometholone acetate; fluoxymesterone; fluprednidene; fluprednisolone; flurandrenolide; fluticasone; fluticasone propionate; formebolone; formestane; formocortal; gestonorone; glyderinine; halcinonide; hyrcanoside; halometasone; halopredone; haloprogesterone; hydrocortiosone cypionate; hydrocortisone; hydrocortisone 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednisolamate; prednisolone; prednisolone 21-hemisuccinate; prednisolone acetate; prednisolone farnesylate; prednisolone hemisuccinate; prednisolone-21(beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone diacetate; triamcinolone hexacetonide; trimegestone; turkesterone; and wortmannin.

Standard recommended dosages for corticosteroids are provided, e.g., in the Merck Manual of Diagnosis & Therapy (17th Ed. MH Beers et al., Merck & Co.) and Physicians' Desk Reference 2003 (57th Ed. Medical Economics Staff et al., Medical Economics Co., 2002). In one embodiment, the dosage of corticosteroid administered is a dosage equivalent to a prednisolone dosage, as defined herein. For example, a low dosage of a corticosteroid may be considered as the dosage equivalent to a low dosage of prednisolone.

Other compounds that may be used as a substitute for or in addition to a corticosteroid in the methods, compositions, and kits of the invention A-348441 (Karo Bio), adrenal cortex extract (GlaxoSmithKline), alsactide (Aventis), amebucort (Schering AG), amelometasone (Taisho), ATSA (Pfizer), bitolterol (Elan), CBP-2011 (InKine Pharmaceutical), cebaracetam (Novartis) CGP-13774 (Kissei), ciclesonide (Altana), ciclometasone (Aventis), clobetasone butyrate (GlaxoSmithKline), cloprednol (Hoffmann-La Roche), collismycin A (Kirin), cucurbitacin E (NIH), deflazacort (Aventis), deprodone propionate (SSP), dexamethasone acefurate (Schering-Plough), dexamethasone linoleate (GlaxoSmithKline), dexamethasone valerate (Abbott), difluprednate (Pfizer), domoprednate (Hoffmann-La Roche), ebiratide (Aventis), etiprednol dicloacetate (IVAX), fluazacort (Vicuron), flumoxonide (Hoffmann-La Roche), fluocortin butyl (Schering AG), fluocortolone monohydrate (Schering AG), GR-250495X (GlaxoSmithKline), halometasone (Novartis), halopredone (Dainippon), HYC-141 (Fidia), icomethasone enbutate (Hovione), itrocinonide (AstraZeneca), L-6485 (Vicuron), Lipocort (Draxis Health), locicortone (Aventis), meclorisone (Schering-Plough), naflocort (Bristol-Myers Squibb), NCX-1015 (NicOx), NCX-1020 (NicOx), NCX-1022 (NicOx), nicocortonide (Yamanouchi), NIK-236 (Nikken Chemicals), NS-126 (SSP), Org-2766 (Akzo Nobel), Org-6632 (Akzo Nobel), P16CM, propylmesterolone (Schering AG), RGH-1113 (Gedeon Richter), rofleponide (AstraZeneca), rofleponide palmitate (AstraZeneca), RPR-106541 (Aventis), RU-26559 (Aventis), Sch-19457 (Schering-Plough), T25 (Matrix Therapeutics), TBI-PAB (Sigma-Tau), ticabesone propionate (Hoffmann-La Roche), tifluadom (Solvay), timobesone (Hoffmann-La Roche), TSC-5 (Takeda), and ZK-73634 (Schering AG).

Non-Steroidal Immunophilin-Dependent Immunosuppressants

The present invention may also involve the administration of a non-steroidal immunophilin-dependent immunosuppressant (NsIDI). In healthy individuals the immune system uses cellular effectors, such as B-cells and T-cells, to target infectious microbes and abnormal cell types while leaving normal cells intact. In individuals with an autoimmune disorder (e.g., diabetes), activated T-cells damage healthy tissues. Calcineurin inhibitors (e.g., cyclosporines, tacrolimus, pimecrolimus), and rapamycin target many types of immunoregulatory cells, including T-cells, and suppress the immune response in autoimmune disorders. Immunosuppressants are particularly useful if the mammal is also receiving an organ, tissue, or cellular implant. Exemplary immunosuppressants are provided below.

Cyclosporines

The cyclosporines are fungal metabolites that comprise a class of cyclic oligopeptides that act as immunosuppressants. Cyclosporine A, and its deuterated analogue ISAtx247, is a hydrophobic cyclic polypeptide consisting of eleven amino acids. Cyclosporine A binds and forms a complex with the intracellular receptor cyclophilin. The cyclosporine/cyclophilin complex binds to and inhibits calcineurin, a $Ca^{2+}$-calmodulin-dependent serine-threonine-specific protein phosphatase. Calcineurin mediates signal transduction events required for T-cell activation (reviewed in Schreiber et al., Cell 70:365-368, 1991). Cyclosporines and their functional and structural analogs suppress the T-cell-dependent immune response by inhibiting antigen-triggered signal transduction. This inhibition decreases the expression of proinflammatory cytokines, such as IL-2.

Many cyclosporines (e.g., cyclosporine A, B, C, D, E, F, G, H, and I) are produced by fungi. Cyclosporine A is a commercially available under the trade name NEORAL from Novartis. Cyclosporine A structural and functional analogs include cyclosporines having one or more fluorinated amino acids (described, e.g., in U.S. Pat. No. 5,227,467); cyclosporines having modified amino acids (described, e.g., in U.S. Pat. Nos. 5,122,511 and 4,798,823); and deuterated cyclosporines, such as ISAtx247 (described in U.S. Patent Publication No. 20020132763). Additional cyclosporine analogs are described in U.S. Pat. Nos. 6,136,357, 4,384,996, 5,284,826, and 5,709,797. Cyclosporine analogs include, but are not limited to, D-Sar ($\alpha$-SMe)$^3$ Val$^2$-DH-Cs (209-825), Allo-Thr-2-Cs, Norvaline-2-Cs, D-Ala (3-acetylamino)-8-Cs, Thr-2-Cs, and D-MeSer-3-Cs, D-Ser (O—$CH_2CH_2$—OH)-8-Cs, and D-Ser-8-Cs, which are described in Cruz et al. (Antimicrob. Agents Chemother. 44:143-149, 2000).

Cyclosporines are highly hydrophobic and readily precipitate in the presence of water (e.g., on contact with body fluids). Methods of providing cyclosporine formulations with improved bioavailability are described in U.S. Pat. Nos. 4,388,307, 6,468,968, 5,051,402, 5,342,625, 5,977,066, and 6,022,852. Cyclosporine microemulsion compositions are described in U.S. Pat. Nos. 5,866,159, 5,916,589, 5,962,014, 5,962,017, 6,007,840, and 6,024,978.

Cyclosporines can be administered either intravenously or orally, but oral administration is preferred. To counteract the hydrophobicity of cyclosporine A, an intravenous cyclosporine A is usually provided in an ethanol-polyoxyethylated castor oil vehicle that must be diluted prior to administration. Cyclosporine A may be provided, e.g., as a microemulsion in a 25 mg or 100 mg tablets, or in a 100 mg/ml oral solution (NEORAL™).

Typically, patient dosage of an oral cyclosporine varies according to the patient's condition, but some standard recommended dosages in prior art treatment regimens are provided herein. Patients undergoing organ transplant (e.g., pancreatic islet transplantation) typically receive an initial dose of oral cyclosporine A in amounts between 12 and 15 mg/kg/day. Dosage is then gradually decreased by 5% per week until a 7-12 mg/kg/day maintenance dose is reached. For intravenous administration, 2-6 mg/kg/day is preferred for most patients. Often cyclosporines are administered in combination with other immunosuppressive agents, such as glucocorticoids. Additional information is provided in Table 3.

TABLE 3

| NsIDIs | |
|---|---|
| Compound | Transplant |
| Cyclosporine A (NEORAL) | ~7-12 mg/kg/day |
| Tacrolimus | 0.1-0.2 mg/kg/day (oral) |
| Pimecrolimus | 40-120 mg/day (oral) |

Tacrolimus

Tacrolimus (PROGRAF, Fujisawa), also known as FK506, is an immunosuppressive agent that targets T-cell intracellular signal transduction pathways. Tacrolimus binds to an intracellular protein FK506 binding protein (FKBP-12) that is not structurally related to cyclophilin (Harding et al. Nature 341:758-7601, 1989; Siekienka et al. Nature 341:755-757, 1989; and Soltoff et al., J. Biol. Chem. 267:17472-17477, 1992). The FKBP/FK506 complex binds to calcineurin and inhibits calcineurin's phosphatase activity. This inhibition prevents the dephosphorylation and nuclear translocation of NFAT, a nuclear component that initiates gene transcription required for lymphokine (e.g., IL-2, gamma interferon) production and T-cell activation. Thus, tacrolimus inhibits T-cell activation.

Tacrolimus is a macrolide antibiotic that is produced by *Streptomyces tsukubaensis*. It suppresses the immune system and prolongs the survival of transplanted organs. It is currently available in oral and injectable formulations. Tacrolimus capsules contain 0.5 mg, 1 mg, or 5 mg of anhydrous tacrolimus within a gelatin capsule shell. The injectable formulation contains 5 mg anhydrous tacrolimus in castor oil and alcohol that is diluted with 9% sodium chloride or 5% dextrose prior to injection. While oral administration is preferred, patients unable to take oral capsules may receive injectable tacrolimus. The initial dose should be administered no sooner than six hours after transplant by continuous intravenous infusion.

Tacrolimus and tacrolimus analogs are described by Tanaka et al., (J. Am. Chem. Soc., 109:5031, 1987), and in U.S. Pat. Nos. 4,894,366, 4,929,611, and 4,956,352. FK506-related compounds, including FR-900520, FR-900523, and FR-900525, are described in U.S. Pat. No. 5,254,562; O-aryl, O-alkyl, O-alkenyl, and O-alkynylmacrolides are described in U.S. Pat. Nos. 5,250,678, 532,248, 5,693,648; amino O-aryl macrolides are described in U.S. Pat. No. 5,262,533; alkylidene macrolides are described in U.S. Pat. No. 5,284,840; N-heteroaryl, N-alkylheteroaryl, N-alkenylheteroaryl, and N-alkynylheteroaryl macrolides are described in U.S. Pat. No. 5,208,241; aminomacrolides and derivatives thereof are described in U.S. Pat. No. 5,208,228; fluoromacrolides are described in U.S. Pat. No. 5,189,042; amino O-alkyl, O-alkenyl, and O-alkynylmacrolides are described in U.S. Pat. No. 5,162,334; and halomacrolides are described in U.S. Pat. No. 5,143,918.

While suggested dosages will vary with a patient's condition, standard recommended dosages used in prior art treatment regimens are provided below. Patients having a transplanted organ typically receive doses of 0.1-0.2 mg/kg/day of oral tacrolimus. Patients being treated for rheumatoid arthritis typically receive 1-3 mg/day oral tacrolimus. For the treatment of psoriasis, 0.01-0.15 mg/kg/day of oral tacrolimus is administered to a patient. Patients receiving oral tacrolimus capsules typically receive the first dose no sooner than six hours after transplant, or eight to twelve hours after intravenous tacrolimus infusion was discontinued. Thus, suggested tacrolimus dosages include 0.005-0.01 mg/kg/day, 0.01-0.03 mg/kg/day, 0.03-0.05 mg/kg/day, 0.05-0.07 mg/kg/day, 0.07-0.10 mg/kg/day, 0.10-0.25 mg/kg/day, or 0.25-0.5 mg/kg/day.

Tacrolimus is extensively metabolized by the mixed-function oxidase system, in particular, by the cytochrome P-450 system. The primary mechanism of metabolism is demethylation and hydroxylation. While various tacrolimus metabolites are likely to exhibit immunosuppressive biological activity, the 13-demethyl metabolite is reported to have the same activity as tacrolimus.

Pimecrolimus and Ascomycin Derivatives

Ascomycin is a close structural analog of FK506 and is a potent immunosuppressant. It binds to FKBP-12 and suppresses its proline rotamase activity. The ascomycin-FKBP complex inhibits calcineurin, a type 2B phosphatase.

Pimecrolimus (also known as SDZ ASM-981) is an 33-epichloro derivative of the ascomycin. It is produced by the strain *Streptomyces hygroscopicus* var. *ascomyceitus*. Like tacrolimus, pimecrolimus (ELIDEL™, Novartis) binds FKBP-12, inhibits calcineurin phosphatase activity, and inhibits T-cell activation by blocking the transcription of early cytokines. In particular, pimecrolimus inhibits IL-2 production and the release of other proinflammatory cytokines.

Pimecrolimus structural and functional analogs are described in U.S. Pat. No. 6,384,073. Pimecrolimus is particularly useful for the treatment of atopic dermatitis. Pimecrolimus is currently available as a 1% cream. While individual dosing will vary with the patient's condition, some standard recommended dosages are provided below. Patients having an organ transplant can be administered 160-240 mg/day of pimecrolimus. Thus, useful dosages of pimecrolimus range between 0.5-5 mg/day, between 5-10 mg/day, between 10-30 mg/day, between 40-80 mg/day, between 80-120 mg/day, or even between 120-200 mg/day.

Rapamycin

Rapamycin (Rapamune® sirolimus, Wyeth) is a cyclic lactone produced by *Steptomyces hygroscopicus*. Rapamycin is an immunosuppressive agent that inhibits T-lymphocyte activation and proliferation. Like cyclosporines, tacrolimus, and pimecrolimus, rapamycin forms a complex with the immunophilin FKBP-12, but the rapamycin-FKBP-12 complex does not inhibit calcineurin phosphatase activity. The rapamycin-immunophilin complex binds to and inhibits the mammalian target of rapamycin (mTOR), a kinase that is required for cell cycle progression. Inhibition of mTOR kinase activity blocks T-lymphocyte proliferation and lymphokine secretion.

Rapamycin structural and functional analogs include mono- and diacylated rapamycin derivatives (U.S. Pat. No. 4,316,885); rapamycin water-soluble prodrugs (U.S. Pat. No. 4,650,803); carboxylic acid esters (PCT Publication No. WO 92/05179); carbamates (U.S. Pat. No. 5,118,678); amide esters (U.S. Pat. No. 5,118,678); biotin esters (U.S. Pat. No. 5,504,091); fluorinated esters (U.S. Pat. No. 5,100,883); acetals (U.S. Pat. No. 5,151,413); silyl ethers (U.S. Pat. No. 5,120,842); bicyclic derivatives (U.S. Pat. No. 5,120,725);

rapamycin dimers (U.S. Pat. No. 5,120,727); O-aryl, O-alkyl, O-alkyenyl and O-alkynyl derivatives (U.S. Pat. No. 5,258, 389); and deuterated rapamycin (U.S. Pat. No. 6,503,921). Additional rapamycin analogs are described in U.S. Pat. Nos. 5,202,332 and 5,169,851.

Everolimus (40-O-(2-hydroxyethyl)rapamycin; CERTICAN™; Novartis) is an immunosuppressive macrolide that is structurally related to rapamycin, and has been found to be particularly effective at preventing acute rejection of organ transplant when given in combination with cyclosporin A.

Rapamycin is currently available for oral administration in liquid and tablet formulations. RAPAMUNE™ liquid contains 1 mg/mL rapamycin that is diluted in water or orange juice prior to administration. Tablets containing 1 or 2 mg of rapamycin are also available. Rapamycin is preferably given once daily as soon as possible after transplantation. It is absorbed rapidly and completely after oral administration. Typically, patient dosage of rapamycin varies according to the patient's condition, but some standard recommended dosages are provided below. The initial loading dose for rapamycin is 6 mg. Subsequent maintenance doses of 2 mg/day are typical. Alternatively, a loading dose of 3 mg, 5 mg, 10 mg, 15 mg, 20 mg, or 25 mg can be used with a 1 mg, 3 mg, 5 mg, 7 mg, or 10 mg per day maintenance dose. In patients weighing less than 40 kg, rapamycin dosages are typically adjusted based on body surface area; generally a 3 mg/m$^2$/day loading dose and a 1-mg/m$^2$/day maintenance dose is used.

Conjugates

If desired, the drugs used in any of the combinations described herein may be covalently attached to one another to form a conjugate of formula XXX.

(A)-(L)-(B)　　　　　　　　　　　　　　　(XXX)

In formula XXX, (A) is a drug listed on Table 1 covalently tethered via a linker (L) to (B), a sulfonylurea, a non-sulfonylurea secretagogue, insulin, an insulin analog, glucagon-like peptide, exendin-4, YM178, FK614, a dipeptidyl peptidase IV inhibitor, biguanide, thiazalidinedione, an alpha-glucosidase inhibitor, an immunosuppressant, an immunomodulator, an angiotensin converting enzyme (ACE) inhibitor, an angiotensin II receptor blocker, an antioxidant, or a second drug listed on Table 1.

Conjugates of the invention can be administered to a subject by any route and for the treatment of any disease described herein.

The conjugates of the invention can be prodrugs, releasing drug (A) and drug (B) upon, for example, cleavage of the conjugate by intracellular and extracellular enzymes (e.g., amidases, esterases, and phosphatases). The conjugates of the invention can also be designed to largely remain intact in vivo, resisting cleavage by intracellular and extracellular enzymes. The degradation of the conjugate in vivo can be controlled by the design of linker (L) and the covalent bonds formed with drug (A) and drug (B) during the synthesis of the conjugate.

Conjugates can be prepared using techniques familiar to those skilled in the art. For example, the conjugates can be prepared using the methods disclosed in G. Hermanson, Bioconjugate Techniques, Academic Press, Inc., 1996. The synthesis of conjugates may involve the selective protection and deprotection of alcohols, amines, ketones, sulfhydryls or carboxyl functional groups of drug (A), the linker, and/or drug (B). For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxyls include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxytrityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, sulfhydryl, and carboxyl functionalities and the conditions required for their removal are provided in detail in T. W. Green and P. G. M. Wuts, Protective Groups in Organic Synthesis ($2^{nd}$ Ed.), John Wiley & Sons, 1991 and P. J. Kocienski, Protecting Groups, Georg Thieme Verlag, 1994. Additional synthetic details are provided below.

Linkers

The linker component of the invention is, at its simplest, a bond between drug (A) and drug (B), but typically provides a linear, cyclic, or branched molecular skeleton having pendant groups covalently linking drug (A) to drug (B).

Thus, linking of drug (A) to drug (B) is achieved by covalent means, involving bond formation with one or more functional groups located on drug (A) and drug (B). Examples of chemically reactive functional groups which may be employed for this purpose include, without limitation, amino, hydroxyl, sulfhydryl, carboxyl, carbonyl, carbohydrate groups, vicinal diols, thioethers, 2-aminoalcohols, 2-aminothiols, guanidinyl, imidazolyl, and phenolic groups.

The covalent linking of drug (A) and drug (B) may be effected using a linker which contains reactive moieties capable of reaction with such functional groups present in drug (A) and drug (B). For example, an amine group of drug (A) may react with a carboxyl group of the linker, or an activated derivative thereof, resulting in the formation of an amide linking the two.

Examples of moieties capable of reaction with sulfhydryl groups include α-haloacetyl compounds of the type $XCH_2CO$— (where X=Br, Cl or I), which show particular reactivity for sulfhydryl groups, but which can also be used to modify imidazolyl, thioether, phenol, and amino groups as described by Gurd, Methods Enzymol. 11:532 (1967). N-Maleimide derivatives are also considered selective towards sulfhydryl groups, but may additionally be useful in coupling to amino groups under certain conditions. Reagents such as 2-iminothiolane (Traut et al., Biochemistry 12:3266 (1973)), which introduce a thiol group through conversion of an amino group, may be considered as sulfhydryl reagents if linking occurs through the formation of disulphide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type XCH$_2$CO— (where X=Cl, Br or I), for example, as described by Wong *Biochemistry* 24:5337 (1979);

(ii) N-maleimide derivatives, which may react with amino groups either through a Michael type reaction or through acylation by addition to the ring carbonyl group, for example, as described by Smyth et al., *J. Am. Chem. Soc.* 82:4600 (1960) and *Biochem. J.* 91:589 (1964);

(iii) aryl halides such as reactive nitrohaloaromatic compounds;

(iv) alkyl halides, as described, for example, by McKenzie et al., *J. Protein Chem.* 7:581 (1988);

(v) aldehydes and ketones capable of Schiff's base formation with amino groups, the adducts formed usually being stabilized through reduction to give a stable amine;

(vi) epoxide derivatives such as epichlorohydrin and bisoxiranes, which may react with amino, sulfhydryl, or phenolic hydroxyl groups;

(vii) chlorine-containing derivatives of s-triazines, which are very reactive towards nucleophiles such as amino, sulfhydryl, and hydroxyl groups;

(viii) aziridines based on s-triazine compounds detailed above, e.g., as described by Ross, *J. Adv. Cancer Res.* 2:1 (1954), which react with nucleophiles such as amino groups by ring opening;

(ix) squaric acid diethyl esters as described by Tietze, *Chem. Ber.* 124:1215 (1991); and (x) α-haloalkyl ethers, which are more reactive alkylating agents than normal alkyl halides because of the activation caused by the ether oxygen atom, as described by Benneche et al., *Eur. J. Med. Chem.* 28:463 (1993).

Representative amino-reactive acylating agents include:

(i) isocyanates and isothiocyanates, particularly aromatic derivatives, which form stable urea and thiourea derivatives respectively;

(ii) sulfonyl chlorides, which have been described by Herzig et al., *Biopolymers* 2:349 (1964);

(iii) acid halides;

(iv) active esters such as nitrophenylesters or N-hydroxysuccinimidyl esters;

(v) acid anhydrides such as mixed, symmetrical, or N-carboxyanhydrides;

(vi) other useful reagents for amide bond formation, for example, as described by M. Bodansky, Principles of Peptide Synthesis, Springer-Verlag, 1984;

(vii) acylazides, e.g. wherein the azide group is generated from a preformed hydrazide derivative using sodium nitrite, as described by Wetz et al., *Anal. Biochem.* 58:347 (1974); and (viii) imidoesters, which form stable amidines on reaction with amino groups, for example, as described by Hunter and Ludwig, *J. Am. Chem. Soc.* 84:3491 (1962).

Aldehydes and ketones may be reacted with amines to form Schiff's bases, which may advantageously be stabilized through reductive amination. Alkoxylamino moieties readily react with ketones and aldehydes to produce stable alkoxamines, for example, as described by Webb et al., in *Bioconjugate Chem.* 1:96 (1990).

Examples of reactive moieties capable of reaction with carboxyl groups include diazo compounds such as diazoacetate esters and diazoacetamides, which react with high specificity to generate ester groups, for example, as described by Herriot, *Adv. Protein Chem.* 3:169 (1947). Carboxyl modifying reagents such as carbodiimides, which react through O-acylurea formation followed by amide bond formation, may also be employed.

It will be appreciated that functional groups in drug (A) and/or drug (B) may, if desired, be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of drug (A) with a reactive chemical group of drug (B) without introducing additional linking material may, if desired, be used in accordance with the invention.

Most commonly, however, the linker will include two or more reactive moieties, as described above, connected by a spacer element. The presence of such a spacer permits bifunctional linkers to react with specific functional groups within drug (A) and drug (B), resulting in a covalent linkage between the two. The reactive moieties in a linker may be the same (homobifunctional linker) or different (heterobifunctional linker, or, where several dissimilar reactive moieties are present, heteromultifunctional linker), providing a diversity of potential reagents that may bring about covalent attachment between drug (A) and drug (B).

Spacer elements in the linker typically consist of linear or branched chains and may include a $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, or $C_{1-10}$ heteroalkyl.

In some instances, the linker is described by formula (XXXI):

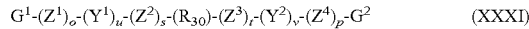

$$G^1\text{-}(Z^1)_o\text{-}(Y^1)_u\text{-}(Z^2)_s\text{-}(R_{30})\text{-}(Z^3)_t\text{-}(Y^2)_v\text{-}(Z^4)_p\text{-}G^2 \quad (XXXI)$$

In formula (XXXI), $G^1$ is a bond between drug (A) and the linker; $G^2$ is a bond between the linker and drug (B); $Z^1$, $Z^2$, $Z^3$, and $Z^4$ each, independently, is selected from O, S, and NR$_{31}$; R$_{31}$ is hydrogen, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl; $Y^1$ and $Y^2$ are each, independently, selected from carbonyl, thiocarbonyl, sulphonyl, or phosphoryl; o, p, s, t, u, and v are each, independently, 0 or 1; and R$_{30}$ is a $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, or $C_{1-10}$ heteroalkyl, or a chemical bond linking $G^1$-$(Z^1)_o$-$(Y^1)_u$-$(Z^2)_n$- to -$(Z^3)_t$-$(Y^2)_v$-$(Z^4)_p$-$G^2$. Examples of homobifunctional linkers useful in the preparation of conjugates of the invention include, without limitation, diamines and diols selected from ethylenediamine, propylenediamine and hexamethylenediamine, ethylene glycol, diethylene glycol, propylene glycol, 1,4-butanediol, 1,6-hexanediol, cyclohexanediol, and polycaprolactone diol.

Formulation

Any of the agents employed according to the present invention may be contained in any appropriate amount in any suitable carrier substance, and is generally present in an amount of 1-95% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

If more than one agent is employed, each agent may be formulated in a variety of ways that are known in the art. Desirably, the agents are formulated together for the simultaneous or near simultaneous administration of the agents. Such co-formulated compositions can include the two agents formulated together in the same pill, capsule, liquid, etc. It is to be understood that, when referring to the formulation of such combinations, the formulation technology employed is also useful for the formulation of the individual agents of the combination, as well as other combinations of the invention. By using different formulation strategies for different agents, the pharmacokinetic profiles for each agent can be suitably matched.

The individually or separately formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Dosages

Generally, when administered to a human, the dosage of any of the agents of the combination of the invention will depend on the nature of the agent, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in the combination can, independently, be one to four times daily for one day to one year, and may even be for the life of the patient. Chronic, long-term administration will be indicated in many cases.

Additional Applications

If desired, the compounds of the invention may be employed in mechanistic assays to determine whether other combinations, or single agents, are as effective as the combination in treating, reducing, or preventing metabolic disorders (e.g., diabetes or any of its associated conditions) using assays generally known in the art, examples of which are described herein. For example, candidate compounds may be tested, alone or in combination (e.g., with an agent that reduces glucose levels, such as those described herein) and applied to adipocytes or muscle cells in the presence of insulin and glucose. After a suitable time, these cells are examined for glucose uptake. An increase in glucose uptake identifies a candidate compound or combination of agents as an effective agent to treat, prevent, or reduce a metabolic disorder.

The agents of the invention are also useful tools in elucidating mechanistic information about the biological pathways involved in glucose transport and glucose utilization. Such information can lead to the development of new combinations or single agents for treating, preventing, or reducing diabetes. Methods known in the art to determine biological pathways can be used to determine the pathway, or network of pathways affected by contacting cells (e.g., adipocytes, muscle cells, or any cells that utilizes glucose as a source of energy) in the presence of insulin and glucose or by contacting pancreatic cells (any cell that has the ability to produce insulin) with the compounds of the invention. Such methods can include, analyzing cellular constituents that are expressed or repressed after contact with the compounds of the invention as compared to untreated, positive or negative control compounds, and/or new single agents and combinations, or analyzing some other metabolic activity of the cell such as enzyme activity, nutrient uptake, and proliferation. Cellular components analyzed can include gene transcripts, and protein expression. Suitable methods can include standard biochemistry techniques, radiolabeling the compounds of the invention (e.g., $^{14}C$ or $^{3}H$ labeling), and observing the compounds binding to proteins, e.g. using 2D gels, gene expression profiling. Once identified, such compounds can be used in in vivo models (e.g., NOD mice) to further validate the tool or develop new agents or strategies to treat, prevent, or reduce metabolic disorders.

As indicated above, the methods of this invention may also be used prophylactically, in patients who are an increased risk of developing diabetes or a condition associated with diabetes. Risk factors include for example, family history of diabetes or obesity conditions, quality of nutrition, level of physical activity, presence of molecular markers of diabetes, age, race, or sex. Patients affected with other non-related disorders may also be predisposed to secondary diabetes.

Exemplary Candidate Compounds

Peptide Moieties

Peptides, peptide mimetics, and peptide fragments (whether natural, synthetic or chemically modified) are suitable for use in practicing the invention. Exemplary inhibitors include compounds that reduce the amount of target protein or RNA levels (e.g., antisense compounds, dsRNA, ribozymes) and compounds that compete with endogenous mitotic kinesins or protein tyrosine phosphatases for binding partners (e.g., dominant negative proteins or polynucleotides encoding the same).

Antisense Compounds

The biological activity of any enzyme that increases blood glucose concentration can be reduced through the use of an antisense compound directed to RNA encoding the target protein. Antisense compounds that reduce expression of signaling molecules can be identified using standard techniques. For example, accessible regions of the target the mRNA of the target enzyme can be predicted using an RNA secondary structure folding program such as MFOLD (M. Zuker, D. H. Mathews & D. H. Turner, Algorithms and Thermodynamics for RNA Secondary Structure Prediction: A Practical Guide.

In: RNA Biochemistry and Biotechnology, J. Barciszewski & B. F. C. Clark, eds., NATO ASI Series, Kluwer Academic Publishers, (1999)). Sub-optimal folds with a free energy value within 5% of the predicted most stable fold of the mRNA are predicted using a window of 200 bases within which a residue can find a complimentary base to form a base pair bond. Open regions that do not form a base pair are summed together with each suboptimal fold and areas that are predicted as open are considered more accessible to the binding to antisense nucleobase oligomers. Other methods for antisense design are described, for example, in U.S. Pat. No. 6,472,521, Antisense Nucleic Acid Drug Dev. 1997 7:439-444, Nucleic Acids Research 28:2597-2604, 2000, and Nucleic Acids Research 31:4989-4994, 2003.

RNA Interference

The biological activity of a signaling molecule can be reduced through the use of RNA interference (RNAi), employing, e.g., a double stranded RNA (dsRNA) or small interfering RNA (siRNA) directed to the signaling molecule in question (see, e.g., Miyamoto et al., Prog. Cell Cycle Res. 5:349-360, 2003; U.S. Patent Application Publication No. 20030157030). Methods for designing such interfering RNAs are known in the art. For example, software for designing interfering RNA is available from Oligoengine (Seattle, Wash.).

Dominant Negative Proteins

One skilled in the art would know how to make dominant negative proteins to the signaling molecules to be targeted. Such dominant negative proteins are described, for example, in Gupta et al., J. Exp. Med., 186:473-478, 1997; Maegawa et al., J. Biol. Chem. 274:30236-30243, 1999; Woodford-Thomas et al., J. Cell Biol. 117:401-414, 1992).

Example 1

An Increase in Insulin-Stimulated Glucose Uptake In Vitro

Differentiated mouse adipocytes were employed to identify combinations of agents that have the ability to increase glucose uptake upon insulin stimulation, as detected by scintillation counting of radiolabelled glucose (using, for example, the Perkin Elmer 1450 Microbeta JET reader). These assays were conducted as follows.

Materials and Methods

Prees Media

Complete media, also referred to as "Prees" media, was prepared as follows. Dulbecco's Modified Eagle's Medium (DMEM) was supplemented with L-glutamine, penicillin-G and streptomycin (pen/strep), and heat-inactivated fetal bovine serum (FBS) (heat inactivated at 65° C. for 30 minutes). Because serum can affect the growth, adherence, and differentiation of cells, any new lot of serum was first tested prior to use. Media was equilibrated in the incubator (5% $CO_2$) until the pH was within the proper range (~7), as indicated by the red/orange color of the indicator dye. If the media became pink (indicating a high pH), we discarded the media as basic conditions can affect cells and denature the insulin used in the differentiation medium-1 (DM1) and the differentiation medium-2 (DM2).

Differentiation Medias

Differentiation media-1 (DM1) was prepared by supplementing DMEM with 10% FBS, L-glutamine, pen/strep, IBMX (375 µM), insulin (120 nM), and dexamethasone (188 nM). Differentiation media-2 (DM2) was prepared by supplementing DMEM with 10% FBS, L-glutamine, pen/strep, and insulin (120 nM).

Preparation of Gelatinized Plates

Cell culture plates were gelatinized as follows. Gelatin (1% w/v in distilled water) was autoclaved and stored at room temperature. The bottom of each cell culture well was covered uniformly in the gelatin solution, ensuring that no bubbles were formed. This solution was removed leaving behind a thin film of gelatin. These plates were left to dry under the tissue culture hood. Plates were next washed with PBS, after which a 0.5% glutaric dialdehyde solution (glutaraldehyde in distilled water) was added to the cell culture wells. After ten minutes, wells were washed twice with DMEM containing pen-strep. Each washing step should last for approximately five minutes.

Cell Culture

3T3-L1 pre-adipocyte cells were split approximately every 2-3 days or upon reaching a confluence of approximately 60%. Overconfluency may affect the ability of these cells to differentiate into adipocytes.

Other Reagents

D-(+)-glucose ("cold" glucose, not radiolabeled) was added to DPBS mix to a final concentration of 10 mM.

Lysis buffer, a mixture of a base (e.g., sodium hydroxide at a final concentration of 0.5N) and a detergent (e.g., sodium dodecyl sulphate (SDS) diluted to a final concentration of 0.1% w/v) was freshly prepared each time (within one to two hours of use). Prior to use, lysis buffer was warmed up to a temperature exceeding that of room temperature for a period of approximately 30 minutes to avoid precipitation of the buffer.

Determination of Glucose Uptake

Pre-adipocyte 3T3-L1 cells were plated at a density of approximately 5000 cells/well (in black NUNC 96 well plate). These cells were differentiated into adipocytes in two separate steps. Initially, cells were cultured in differentiation medium-1 (DM1) (day 1 of adipocyte differentation) for a period of two to three days. DM1 prevents proliferation and induces the expression of adipocyte-specific genes. Cells were next cultured in differentiation medium-2 (DM2) for 3 to 4 days, after which the culture media was replaced by fresh DM2. The glucose uptake assay was performed at day 9-15 of differentiation.

Two days prior to the experiment (at day 7-13 of differentiation), DM2 was removed and replaced with fresh Prees media. Candidate compounds were added at this time, allowing an incubation period of approximately 48 hours. On the day of the experiment, cells (now at day 9 to 15 of differentiation) were serum starved for three hours in DPBS, magnesium sulfate (0.8 mM), and Hepes (10 mM) at pH ~7. After this incubation period, fresh DPBS containing insulin (10 nM) was added to the adipocytes. Fresh DPBS without any insulin were placed on cells that served as a negative control. Following an incubation period of 25 minutes at 37° C., radioactive glucose (labeled with $^{14}C$, at a final concentration of 0.04 mM, ~0.26 µCi $^{14}C$-glucose in each well) was added to the media for a period of 15 minutes at room temperature. Media was next removed and cells were washed thoroughly and lysed. Upon lysis, cells form a small, cloudy mass, detached from the well bottom. 10% glacial acetic acid was added to each well to neutralize the lysis reaction. Scintillation fluid was next added to the wells and the incorporation of glucose was determined by measuring the amount of radioactivity in each well using the MicroBeta plate reader.

The data are shown in Tables 4 and 5, below.

TABLE 4

|  | | Diflunisal (μM) | | | |
| --- | --- | --- | --- | --- | --- |
|  |  | 36 | 18 | 9 | 0 |
| Bezafibrate | 36 | 1.69 | 1.74 | 1.74 | 1.57 |
| (μM) | 18 | 1.67 | 1.62 | 1.57 | 1.37 |
|  | 9 | 1.65 | 1.42 | 1.27 | 1.16 |
|  | 0 | 1.52 | 1.19 | 1.12 | 0.99 |

The average fold increase in insulin-stimulated glucose uptake compared to vehicle treated control was determined. The average of four biological replicates is shown. At all combination doses there is an increase in glucose uptake as compared to the single agents.

TABLE 5

|  | | Bezafibrate (μM) | | | |
| --- | --- | --- | --- | --- | --- |
|  |  | 36 | 18 | 9 | 0 |
| Cinnamic | 12 | 1.46 | 1.36 | 1.23 | 1.10 |
| acid (μM) | 6 | 1.49 | 1.36 | 1.17 | 1.03 |
|  | 3 | 1.30 | 1.26 | 1.10 | 0.98 |
|  | 0 | 1.15 | 1.21 | 0.94 | 0.88 |

The average fold increase in insulin-stimulated glucose uptake compared to vehicle treated control was determined. The average of three biological replicates is shown. At all combination doses there is an increase in glucose uptake as compared to the single agents.

Example 2

The Combination of Bezafibrate and Diflunisal Reduce Insulin Sensitivity in a Rat Model Insulin resistance was induced in male Sprague Dawley rats by four weeks of high fat feeding (60% of calories derived from fat). Drug treatment began one week after initiation of high fat diet. Drugs were administered daily, by oral gavage for a three week period.

Following the three weeks of treatment, animals were fasted for five hours and anesthetized, and blood collected from the inferior vena cava for determination of serum glucose and insulin levels. Insulin sensitivity was determined using the homeostasis model assessment (HOMA).

$$HOMA = \frac{\text{fasting serum glucose} \times \text{fasting serum insulin}}{22.5}$$

Figure 1:
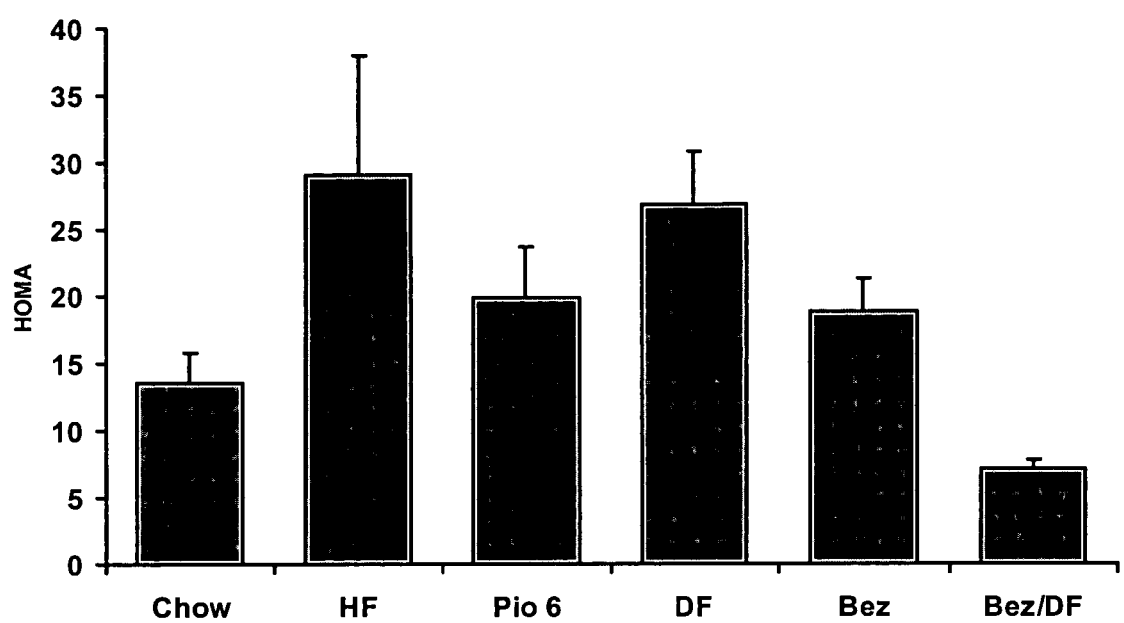
FIG. 1 is a graph showing insulin sensitivity in male Sprague Dawley rats, as determined using the homeostasis model assessment (HOMA). Insulin resistance was induced by four weeks of high fat feeding (60% of calories derived from fat). Drug treatment began one week after initiation of high fat diet. Drugs were administered daily, by oral gavage for a three week period. Following the three weeks of treatment, animals were fasted for five hours and anesthetized, and blood collected from the inferior vena cava for determination of serum glucose and insulin levels. Insulin sensitivity was determined using HOMA.

The results are shown in FIGS. 1-3.

Example 3

Screening Assays Identify Additional Agents that Increase Glucose Uptake by Adipocytes Differentiated mouse adipocytes were employed to identify combinations of agents that have the ability to increase glucose uptake upon insulin stimulation, as detected by scintillation counting of radiolabelled glucose (using, for example, the Perkin Elmer 1450 Microbeta JET reader). These assays were conducted as follows.

Materials and Methods

Prees Media

Complete media, also referred to as "Prees" media, was prepared as follows. Dulbecco's Modified Eagle's Medium (DMEM) was supplemented with L-glutamine, penicillin-G and streptomycin (pen/strep), and heat-inactivated fetal bovine serum (FBS) (heat inactivated at 65° C. for 30 minutes). Because serum can affect the growth, adherence, and differentiation of cells, any new lot of serum was first tested prior to use. Media was equilibrated in the incubator (5% $CO_2$) until the pH was within the proper range (~7), as indicated by the red/orange color of the indicator dye. If the media became pink (indicating a high pH), we discarded the media as basic conditions can affect cells and denature the insulin used in the differentiation medium-1 (DM1) and the differentiation medium-2 (DM2).

Differentiation Medias

Differentiation media-1 (DM1) was prepared by supplementing DMEM with 10% FBS, L-glutamine, pen/strep, IBMX (375 μM), insulin (120 nM), and dexamethasone (188 nM). Differentiation media-2 (DM2) was prepared by supplementing DMEM with 10% FBS, L-glutamine, pen/strep, and insulin (120 nM).

Preparation of Gelatinized Plates

Cell culture plates were gelatinized as follows. Gelatin (1% w/v in distilled water) was autoclaved and stored at room temperature. The bottom of each cell culture well was covered uniformly in the gelatin solution, ensuring that no bubbles were formed. This solution was removed leaving behind a thin film of gelatin. These plates were left to dry under the tissue culture hood. Plates were next washed with PBS, after which a 0.5% glutaric dialdehyde solution (glutaraldehyde in distilled water) was added to the cell culture wells. After ten minutes, wells were washed twice with DMEM containing pen-strep. Each washing step should last for approximately five minutes.

Cell Culture

3T3-L1 pre-adipocyte cells were split approximately every 2-3 days or upon reaching a confluence of approximately 60%. Overconfluency may affect the ability of these cells to differentiate into adipocytes.

Other Reagents

D-(+)-glucose ("cold" glucose, not radiolabeled) was added to DPBS mix to a final concentration of 10 mM.

Lysis buffer, a mixture of a base (e.g., sodium hydroxide at a final concentration of 0.5N) and a detergent (e.g., sodium dodecyl sulphate (SDS) diluted to a final concentration of 0.1% w/v) was freshly prepared each time (within one to two hours of use). Prior to use, lysis buffer was warmed up to a temperature exceeding that of room temperature for a period of approximately 30 minutes to avoid precipitation of the buffer.

Determination of Glucose Uptake

Pre-adipocyte 3T3-L1 cells were plated at a density of approximately 5000 cells/well (in black NUNC 96 well plate). These cells were differentiated into adipocytes in two separate steps. Initially, cells were cultured in differentiation medium-1 (DM1) (day 1 of adipocyte differentiation) for a period of two to three days. DM1 prevents proliferation and induces the expression of adipocyte-specific genes. Cells were next cultured in differentiation medium-2 (DM2) for 3 to 4 days, after which the culture media was replaced by fresh DM2. The glucose uptake assay was performed at day 9-15 of differentiation.

Two days prior to the experiment (at day 7-13 of differentiation), DM2 was removed and replaced with fresh Prees media. Candidate compounds were added at this time, allowing an incubation period of approximately 48 hours. On the day of the experiment, cells (now at day 9 to 15 of differentiation) were serum starved for three hours in DPBS, magnesium sulfate (0.8 mM), and Hepes (10 mM) at pH ~7. After this incubation period, fresh DPBS containing insulin (10 nM) was added to the adipocytes. Fresh DPBS without any insulin were placed on cells that served as a negative control. Following an incubation period of 25 minutes at 37° C., radioactive glucose (labeled with $^{14}C$, at a final concentration of 0.04 mM, ~0.26 µCi $^{14}C$-glucose in each well) was added to the media for a period of 15 minutes at room temperature. Media was next removed and cells were washed thoroughly and lysed. Upon lysis, cells form a small, cloudy mass, detached from the well bottom. 10% glacial acetic acid was added to each well to neutralize the lysis reaction. Scintillation fluid was next added to the wells and the incorporation of glucose was determined by measuring the amount of radioactivity in each well using the MicroBeta plate reader. Compounds that exhibited glucose uptake activity are shown in Table 4. Table 4 shows glucose uptake activity (denoted as F (fold over base) with the standard deviation (sF)) of each of the compounds at various concentrations. S/N denotes the signal over noise ratio.

In another set of experiments, human skeletal myoblasts obtained by the conditional immortalization of cells derived from a non-diabetic subject, were used to screen the effect of a multitude of compounds on glycogen synthesis. For each compound, two doses were tested in triplicate. The vehicle was used as a negative control and insulin was used as a positive control. Prior to treatment, cells were serum-starved for 12 to 18 hours in Ham's F10 medium. Cells were next incubated either with the test compounds or control for a period of two hours in serum-free media containing radiolabeled glucose, after which, glycogen synthesis was measured. The results of these experiments are shown in Table 4 (denoted as Xlsyz).

TABLE 6

| Name | CRx F | CRx sF | CRx S/N | CRx uM | Xlsyz F(L) | Xlsyz sF(L) | Xlsyz S/N (L) | Xlsyz uM(L) | Xlsyz F(H) | Xlsyz sF(H) | Xlsyz S/N (H) | Xlsyz uM(H) |
|---|---|---|---|---|---|---|---|---|---|---|---|---|
| Tetrahydrozoline Hydrochloride | 1.0225 | 0.0755 | 13.54 | 39.5477 | 1.2564 | 0.039 | 32.22 | 4.3938 | 1.6 | 0.1451 | 11.03 | 43.9375 |
| ISOPROTERENOL SULFATE | 1.5553 | 0.0975 | 15.95 | 39.494 | 1.6714 | 0.0815 | 20.51 | 3.2331 | 1.5225 | 0.1165 | 13.07 | 32.3311 |
| Acetyldigitoxin | 0.8077 | 0.1165 | 6.93 | 11.1535 | 1.3016 | 0.0434 | 29.99 | 12.3916 | 1.2593 | 0.047 | 26.79 | 1.2392 |
| NOREPINEPHRINE BITARTRATE | 1.7559 | 0.2784 | 6.31 | 27.797 | 1.3758 | 0.0924 | 14.89 | 3.0882 | 1.4353 | 0.1497 | 9.59 | 30.8825 |
| Dipivefrin Hydrochloride | 1.8856 | 0.113 | 16.69 | 23.2042 | 1.2562 | 0.0375 | 33.50 | 2.6553 | 2.6154 | 0.3631 | 7.20 | 26.5532 |
| Brimonidine | 1.4251 | 0.2061 | 6.91 | 31.4307 | 1.6094 | 0.0966 | 16.66 | 3.492 | 1.2967 | 0.0784 | 16.54 | 34.9195 |
| Epinephrine Bitartrate | 1.6511 | 0.1809 | 9.13 | 9.4304 | 1.511 | 0.1387 | 10.89 | 3.2103 | 1.7681 | 0.1006 | 17.58 | 32.1032 |
| Terbutaline Sulfate | 1.2758 | 0.0854 | 14.94 | 33.7985 | 1.3013 | 0.0271 | 48.02 | 3.755 | 1.4059 | 0.1136 | 12.38 | 37.5501 |
| Homatropine Methylbromide | 1.0613 | 0.074 | 14.34 | 25.0363 | 1.3401 | 0.0401 | 33.42 | 2.7815 | 1.3333 | 0.1324 | 10.07 | 27.8153 |
| Loxapine Hydrochloride | 0.9649 | 0.122 | 7.91 | 18.8457 | 1.4364 | 0.1353 | 10.62 | 2.0938 | 1.2281 | 0.0377 | 32.58 | 20.9376 |
| Ethopropazine Hydrochloride | 0.9375 | 0.1223 | 7.67 | 28.8937 | 1.395 | 0.09 | 15.50 | 3.2101 | 0.8406 | 0.0212 | 39.65 | 32.1009 |
| Candesartan Cilexetil | 1.33 | 0.1416 | 9.39 | 15.9295 | 1.7284 | 0.1165 | 14.84 | 1.7698 | 0.6667 | 0.0223 | 29.90 | 17.6977 |
| Inulin | 1.0249 | 0.0918 | 11.16 | 1.4576 | 1.3377 | 0.1023 | 13.08 | 1.6194 | 1.0089 | 0.0339 | 29.76 | 0.1619 |
| Metaproterenol Hemisulfate Salt | 1.7249 | 0.2108 | 8.18 | 16.8778 | 1.4052 | 0.0959 | 14.65 | 1.7812 | 1.1261 | 0.0292 | 38.57 | 17.8116 |
| Invertase | 1.2175 | 0.1785 | 6.82 | 1.843 | 1.3974 | 0.108 | 12.94 | 2.02 | 0.8561 | 0.0305 | 28.07 | 0.202 |
| Methylergonovine Maleate | 0.5265 | 0.2648 | 1.99 | 20.7485 | 1.2906 | 0.0823 | 15.68 | 2.3052 | 1.05 | 0.0271 | 38.75 | 23.0516 |
| Prostaglandin E | 1.5723 | 0.1088 | 14.45 | 26.0518 | 1.7037 | 0.165 | 10.33 | 2.8944 | 1 | 0.149 | 6.71 | 28.9436 |
| Guanfacine Hydrochloride | 0.6974 | 0.2239 | 3.11 | 31.8616 | 1.4264 | 0.11 | 12.97 | 3.5398 | 1.1364 | 0.0349 | 32.56 | 35.3982 |
| Methacholine Chloride | 1.152 | 0.114 | 10.11 | 47.8331 | 1.3086 | 0.0698 | 18.75 | 5.3143 | 1.0156 | 0.0467 | 21.75 | 53.1426 |
| Digitoxin | 0.8801 | 0.0449 | 19.60 | 11.8851 | 1.3846 | 0.1713 | 8.08 | 13.2043 | 1.146 | 0.0486 | 23.58 | 1.3204 |
| Geranyl Acetate | 0.9527 | 0.0694 | 13.73 | 45.8528 | 1.3523 | 0.1396 | 9.69 | 5.0942 | 0.9 | 0.0642 | 14.02 | 50.9424 |
| Evans Blue | 0.9008 | 0.115 | 7.83 | 9.6492 | 1.3913 | 0.1889 | 7.37 | 10.7202 | 1.0519 | 0.0406 | 25.91 | 1.072 |
| Xylazine Hydrochloride | 1.0978 | 0.081 | 13.55 | 51.1733 | 1.3401 | 0.0537 | 24.96 | 5.6854 | 1.0857 | 0.0521 | 20.84 | 56.8536 |
| Oleandomycin | 1.1002 | 0.0811 | 13.57 | 11.5675 | 1.6271 | 0.2313 | 7.03 | 12.8515 | 0.9744 | 0.0403 | 24.18 | 1.2852 |
| Prazosin Hydrochloride | 1.2437 | 0.1464 | 8.50 | 21.4358 | 1.3333 | 0.1184 | 11.26 | 2.3815 | 0.7021 | 0.0264 | 26.59 | 23.8152 |
| Tinidazole | 1.0177 | 0.0646 | 15.75 | 36.3967 | 1.2177 | 0.1579 | 7.71 | 4.0437 | 1.0588 | 0.066 | 16.04 | 40.4367 |
| Enalaprilat | 0.992 | 0.1543 | 6.43 | 26.0636 | 1.2739 | 0.0814 | 15.65 | 2.8957 | 0.8333 | 0.0692 | 12.04 | 28.9567 |
| Tannic Acid | 0.8674 | 0.0779 | 11.13 | 5.2909 | 1.2949 | 0.1048 | 12.36 | 5.8782 | 1.0522 | 0.0219 | 48.05 | 0.5878 |
| Azathioprine | 1.7493 | 0.2205 | 7.93 | 37.0961 | 1.2275 | 0.0948 | 12.95 | 3.6062 | 1.0938 | 0.0352 | 31.07 | 36.062 |
| Ritodrine Hydrochloride | 1.5011 | 0.1595 | 9.41 | 27.7977 | 1.2121 | 0.0445 | 27.24 | 3.0883 | 1.039 | 0.0563 | 18.45 | 30.8833 |
| Guaiacol | 1.0722 | 0.062 | 17.29 | 72.5294 | 1.2105 | 0.0801 | 15.11 | 5.6529 | 0.9873 | 0.028 | 35.26 | 56.5291 |
| Eucalyptol | 1.1325 | 0.1543 | 7.34 | 4948.67 | 1.2047 | 0.1552 | 7.76 | 549.797 | 1.038 | 0.0387 | 26.82 | 5497.97 |
| Promethazine Hydrochloride | 0.9391 | 0.1273 | 7.38 | 28.0489 | 1.2585 | 0.18 | 6.99 | 3.1162 | 0.5797 | 0.0416 | 13.94 | 31.1624 |
| METHANTHELINE BROMIDE | 1.2479 | 0.1282 | 9.73 | 23.0738 | 1.219 | 0.1438 | 8.48 | 2.5635 | 1.1136 | 0.0301 | 37.00 | 25.6349 |
| METHDILAZINE | 0.9361 | 0.1008 | 9.29 | 31.6248 | 1.2127 | 0.0957 | 12.67 | 3.5135 | 0.75 | 0.0258 | 29.07 | 35.1351 |
| Glutamic Acid Hydrochloride | 0.964 | 0.2332 | 4.13 | 43.2463 | 1.2292 | 0.0384 | 32.01 | 4.8047 | 0.9535 | 0.0658 | 14.49 | 48.0466 |

TABLE 6-continued

| Name | CRx F | CRx sF | CRx S/N | CRx uM | Xlsyz F(L) | Xlsyz sF(L) | Xlsyz S/N (L) | Xlsyz uM(L) | Xlsyz F(H) | Xlsyz sF(H) | Xlsyz S/N (H) | Xlsyz uM(H) |
|---|---|---|---|---|---|---|---|---|---|---|---|---|
| Ergoloid Mesylates | 1.1518 | 0.1728 | 6.67 | 21.2536 | 1.2045 | 0.0227 | 53.06 | 1.5158 | 1.1095 | 0.0288 | 38.52 | 15.1584 |
| QUINACRINE | 1.0058 | 0.1727 | 5.82 | 20.5561 | 1.2378 | 0.0468 | 26.45 | 2.2838 | 1.046 | 0.0843 | 12.41 | 22.8378 |
| Meclofenoxate | 1.1681 | 0.1143 | 10.22 | 34.8777 | 1.2103 | 0.0548 | 22.09 | 3.8749 | 1.0625 | 0.0287 | 37.02 | 38.7492 |
| GENISTEIN | 0.4522 | 0.0432 | 10.47 | 33.312 | 1.2013 | 0.0438 | 27.43 | 3.701 | 0.7857 | 0.0355 | 22.13 | 37.0096 |
| Pergolide Mesylate | 1.1326 | 0.1253 | 9.04 | 21.9213 | 1.2698 | 0.1331 | 9.54 | 2.4355 | 1.039 | 0.0425 | 24.45 | 24.3546 |
| Triflupromazine Hydrochloride | 0.9717 | 0.1634 | 5.95 | 23.1445 | 1.2443 | 0.0686 | 18.14 | 2.5714 | 0.2479 | 0.0202 | 12.27 | 25.7136 |
| Levocabastine Hydrochloride | 1.2727 | 0.1069 | 11.91 | 19.6956 | 1.2127 | 0.0791 | 15.33 | 2.1882 | 0.9667 | 0.0687 | 14.07 | 21.8818 |
| Hydroxypropyl Cellulose | 1.0957 | 0.0531 | 20.63 | 1.9082 | 1.2583 | 0.1044 | 12.05 | 2.12 | 1.107 | 0.0519 | 21.33 | 0.212 |
| Oxybutynin Chloride | 1.0483 | 0.1851 | 5.66 | 23.0734 | 1.0847 | 0.0483 | 22.46 | 2.5634 | 1.5652 | 0.1325 | 11.81 | 25.6345 |
| DOXAPRAM HYDROCHLORIDE | 1.1028 | 0.0713 | 15.47 | 21.6188 | 0.9091 | 0.0375 | 24.24 | 2.4018 | 1.4615 | 0.2139 | 6.83 | 24.0185 |
| Pyrilamine Maleate | 1.1294 | 0.0933 | 12.11 | 24.66 | 1.1603 | 0.0329 | 35.27 | 2.7397 | 1.3778 | 0.0901 | 15.29 | 27.3973 |
| LEAD DIETHYLDITHIO-CARBAMATE | 1.524 | 0.4049 | 3.76 | 21.9875 | 1.064 | 0.0607 | 17.53 | 2.4428 | 1.2527 | 0.0391 | 32.04 | 24.4281 |
| Dimenhydrinate | 1.1102 | 0.0697 | 15.93 | 19.7254 | 0.9571 | 0.0366 | 26.15 | 2.1915 | 1.5385 | 0.1913 | 8.04 | 21.9149 |
| Bamethan | 1.1895 | 0.1516 | 7.85 | 17.7718 | 0.9106 | 0.0412 | 22.10 | 1.9744 | 1.3846 | 0.1387 | 9.98 | 19.7445 |
| Dyclonine Hydrochloride | 1.1238 | 0.1232 | 9.12 | 29.5519 | 0.9339 | 0.0334 | 27.96 | 3.2832 | 1.9231 | 0.2533 | 7.59 | 32.8322 |
| Dopamine Hydrochloride | 1.1203 | 0.1517 | 7.38 | 47.4731 | 1.0909 | 0.0756 | 14.43 | 5.2743 | 2 | 0.2348 | 8.52 | 52.7426 |
| Spectinomycin | 1.0474 | 0.1049 | 9.98 | 25.0888 | 1.1245 | 0.0244 | 46.09 | 2.7874 | 1.2881 | 0.0819 | 15.73 | 27.8737 |
| Acetohexamide | 1.0591 | 0.1317 | 8.04 | 27.7463 | 1.0179 | 0.0816 | 12.47 | 3.0826 | 1.3939 | 0.1572 | 8.87 | 30.8261 |
| DL-5-Hydroxytryptophan | 1.0187 | 0.0972 | 10.48 | 40.876 | 1.1353 | 0.0645 | 17.60 | 4.5413 | 1.2903 | 0.0608 | 21.22 | 45.4133 |
| Pioglitazone Hydrochloride | 2.1107 | 0.2432 | 8.68 | 7.6519 | 1.0848 | 0.0538 | 20.16 | 2.5967 | 1.8586 | 0.0109 | 170.51 | 2.5504 |
| Doxylamine Succinate | 1.1094 | 0.0546 | 20.32 | 24.5584 | 0.9643 | 0.0367 | 26.28 | 2.7284 | 1.7692 | 0.2447 | 7.23 | 27.2844 |
| Phensuximide | 1.1431 | 0.0842 | 13.58 | 48.5249 | 1 | 0.0276 | 36.23 | 5.3911 | 1.3333 | 0.1003 | 13.29 | 53.9112 |
| Melphalan | 1.398 | 0.1619 | 8.63 | 27.6151 | 0.9691 | 0.0714 | 13.57 | 3.068 | 1.2982 | 0.0324 | 40.07 | 30.6803 |
| Phenylpropanolamine Hydrochloride | 1.077 | 0.1579 | 6.82 | 49.8718 | 0.9313 | 0.0232 | 40.14 | 5.5408 | 1.4222 | 0.1019 | 13.96 | 55.4076 |
| Acetylcholine Chloride | 1.0512 | 0.1161 | 9.05 | 50.5279 | 1.1605 | 0.0689 | 16.84 | 5.6136 | 1.3305 | 0.0637 | 20.89 | 5.7788 |
| Carbamazepine | 0.7464 | 0.1508 | 4.95 | 41.9001 | 1.0739 | 0.0482 | 22.28 | 4.6551 | 1.4211 | 0.1096 | 12.97 | 46.551 |
| Doxycycline | 0.447 | 0.1142 | 3.91 | 19.0911 | 1.0579 | 0.0288 | 36.73 | 2.121 | 1.7692 | 0.3167 | 5.59 | 21.2102 |
| Phenylephrine Hydrochloride | 1.2537 | 0.089 | 14.09 | 44.187 | 1.1789 | 0.0482 | 24.46 | 4.9092 | 1.6061 | 0.1069 | 15.02 | 49.0918 |
| Diclofenac Sodium | 1.3966 | 0.0673 | 20.75 | 30.3169 | 1.1322 | 0.0345 | 32.82 | 3.458 | 1.4615 | 0.1966 | 7.43 | 34.5803 |
| Acetaminophen | 1.021 | 0.1744 | 5.85 | 60.1251 | 1.0089 | 0.0416 | 24.25 | 6.6799 | 1.6154 | 0.141 | 11.46 | 66.7989 |
| Carbinoxamine Maleate | 0.7798 | 0.1566 | 4.98 | 21.8995 | 1 | 0.0536 | 18.66 | 2.433 | 1.6842 | 0.1255 | 13.42 | 24.3303 |
| Diphenhydramine Hydrochloride | 0.931 | 0.1519 | 6.13 | 31.1546 | 0.9714 | 0.0331 | 29.35 | 3.4613 | 1.9231 | 0.4585 | 4.19 | 34.6127 |
| Oxymetazoline Hydrochloride | 0.8959 | 0.1035 | 8.66 | 35.4664 | 1.1333 | 0.0621 | 18.25 | 3.4704 | 1.3623 | 0.1591 | 8.56 | 34.7035 |
| Imipramine Hydrochloride | 0.8539 | 0.0501 | 17.04 | 28.403 | 1.003 | 0.0839 | 11.95 | 3.1556 | 1.3218 | 0.0693 | 19.07 | 31.5557 |
| Phenacemide | 1.0254 | 0.0733 | 13.99 | 53.5407 | 1 | 0.0247 | 40.49 | 5.9484 | 1.3333 | 0.0993 | 13.43 | 59.4837 |
| Carisoprodol | 1.1305 | 0.0708 | 15.97 | 35.9621 | 1.0992 | 0.04 | 27.48 | 3.9954 | 1.3846 | 0.1515 | 9.14 | 39.9539 |
| Pilocarpine Hydrochloride | 0.8768 | 0.1514 | 5.79 | 37.8869 | 1.187 | 0.0834 | 14.23 | 4.2092 | 1.2889 | 0.0883 | 14.60 | 42.0924 |
| Acetrizoate Sodium | 1.2587 | 0.0957 | 13.15 | 15.7065 | 0.9494 | 0.0464 | 20.46 | 1.745 | 1.3158 | 0.115 | 11.44 | 17.4499 |
| Hydrosocobalamin | 1.1725 | 0.215 | 5.45 | 6.752 | 1.1068 | 0.0352 | 31.44 | 7.5015 | 1.2416 | 0.1306 | 9.51 | 0.7501 |
| Calcium Chloride | 0.7358 | 0.2489 | 2.96 | 83.8859 | 1.0714 | 0.0441 | 24.29 | 9.3197 | 1.2121 | 0.1806 | 6.71 | 93.1973 |
| Cupric Chloride | 1.3661 | 0.0795 | 17.18 | 53.3191 | 1.0643 | 0.0326 | 32.65 | 5.9238 | 1.25 | 0.1173 | 10.66 | 59.2375 |
| Vincamine | 0.8026 | 0.0952 | 8.43 | 25.3976 | 1.1446 | 0.0346 | 33.08 | 2.8217 | 1.2619 | 0.0733 | 17.22 | 28.2167 |
| Acetohydroxamic Acid | 1.0424 | 0.083 | 12.56 | 130.639 | 1.0272 | 0.0446 | 23.03 | 14.514 | 1.3333 | 0.1459 | 9.14 | 145.14 |
| Dirithromycin | 1.0697 | 0.0698 | 15.33 | 11.8561 | 0.9862 | 0.03 | 32.87 | 1.3172 | 1.2533 | 0.0543 | 23.08 | 13.1721 |
| Sulfamethizole | 1.0749 | 0.0786 | 13.68 | 33.9657 | 1.101 | 0.0285 | 38.63 | 3.7736 | 1.2 | 0.0806 | 14.89 | 37.7358 |
| Ammonium Chloride | 0.8881 | 0.1503 | 5.91 | 173.288 | 0.8482 | 0.0444 | 19.10 | 19.2523 | 1.2105 | 0.0912 | 13.27 | 192.523 |
| Tolazoline Hydrochloride | 0.967 | 0.0701 | 13.79 | 47.5899 | 0.9615 | 0.0324 | 29.68 | 5.2872 | 1.2469 | 0.0997 | 12.51 | 52.8724 |
| Diphenidol Hydrochloride | 1.0194 | 0.1118 | 9.12 | 26.2819 | 0.9781 | 0.0357 | 27.40 | 2.9199 | 1.3846 | 0.3815 | 3.63 | 29.1992 |
| Bismuth Subsalicylate | 1.69 | 0.1409 | 11.99 | 24.8575 | 1.0089 | 0.0428 | 23.57 | 3.1759 | 1.2105 | 0.1328 | 9.12 | 31.7592 |
| PHENYTOIN | 1.1755 | 0.1697 | 6.93 | 35.6754 | 0.9796 | 0.0345 | 28.39 | 3.9635 | 1.2174 | 0.0874 | 13.93 | 39.6354 |
| Dicloxacillin Sodium | 1.0042 | 0.1082 | 9.28 | 18.6968 | 1.0511 | 0.068 | 15.46 | 2.0772 | 1.3846 | 0.1962 | 7.06 | 20.7721 |
| Indocyanine Green | 0.8824 | 0.1506 | 5.86 | 12.0364 | 1.0603 | 0.079 | 13.42 | 1.3372 | 1.2 | 0.0405 | 29.63 | 13.3724 |
| HEXYLCAINE HYDROCHLORIDE | 1.0422 | 0.0802 | 13.00 | 30.8602 | 1.1545 | 0.0663 | 17.41 | 3.4286 | 1.2121 | 0.0947 | 12.80 | 34.2857 |
| AMANTADINE HYDROCHLORIDE | 0.618 | 0.0917 | 6.74 | 47.9536 | 0.8699 | 0.0666 | 13.06 | 5.3276 | 1.2308 | 0.1149 | 10.71 | 53.2765 |
| Orphenadrine Citrate | 0.9749 | 0.1018 | 9.58 | 20.0887 | 0.9704 | 0.0683 | 14.21 | 2.2318 | 1.2174 | 0.0661 | 18.42 | 22.3185 |

TABLE 6-continued

| Name | CRx F | CRx sF | CRx S/N | CRx uM | Xlsyz F(L) | Xlsyz sF(L) | Xlsyz S/N (L) | Xlsyz uM(L) | Xlsyz F(H) | Xlsyz sF(H) | Xlsyz S/N (H) | Xlsyz uM(H) |
|---|---|---|---|---|---|---|---|---|---|---|---|---|
| Diflunisal | 1.5694 | 0.0744 | 21.09 | 36.8314 | 0.9421 | 0.0315 | 29.91 | 4.0767 | 1.2308 | 0.1346 | 9.14 | 40.7674 |
| DIPHEMANIL METHYLSULFATE | 1.2078 | 0.0672 | 17.97 | 24.5269 | 0.9708 | 0.0573 | 16.94 | 2.7249 | 1.2308 | 0.2763 | 4.45 | 27.2494 |
| Acetazolamide | 0.8994 | 0.1774 | 5.07 | 41.3183 | 1.0268 | 0.0421 | 24.39 | 4.5905 | 1.3077 | 0.2004 | 6.53 | 45.9046 |
| Sulfasomidine | 1.1803 | 0.0729 | 16.19 | 32.6659 | 1.0165 | 0.0312 | 32.58 | 3.6292 | 1.3077 | 0.1693 | 7.72 | 36.2918 |
| Diatrizoate Sodium | 0.9858 | 0.0493 | 20.00 | 16.2778 | 0.9562 | 0.0343 | 27.88 | 1.8085 | 1.3077 | 0.15 | 8.72 | 18.0846 |
| Cefamandole Nafate | 1.2353 | 0.0735 | 16.81 | 17.914 | 1.0165 | 0.0397 | 25.60 | 1.9902 | 1.25 | 0.109 | 11.47 | 19.9024 |
| Arbutin | 1.0786 | 0.1077 | 10.01 | 36.6911 | 1.056 | 0.0489 | 21.60 | 4.0764 | 1.2045 | 0.0495 | 24.33 | 40.7639 |
| Iopromide | 0.8499 | 0.0662 | 12.84 | 11.7205 | 0.9852 | 0.0316 | 31.18 | 1.3022 | 1.25 | 0.0825 | 15.15 | 13.0215 |
| Phenylbutazone | 1.2098 | 0.0872 | 13.87 | 29.4777 | 0.9675 | 0.0642 | 15.07 | 3.275 | 1.2444 | 0.0894 | 13.92 | 32.7497 |
| SUCCINYLCHOLINE | 1.0409 | 0.1125 | 9.25 | 23.7879 | 0.9577 | 0.0383 | 25.01 | 2.6428 | 1.2231 | 0.095 | 12.87 | 26.4284 |
| Captopril | 0.662 | 0.3 | 2.21 | 44.321 | 1.0804 | 0.0503 | 21.48 | 4.9241 | 1.2632 | 0.109 | 11.59 | 49.2407 |
| Iohenoxic Acid | 1.0641 | 0.0986 | 10.79 | 16.3681 | 1.0504 | 0.0382 | 27.50 | 1.8185 | 1.2119 | 0.0796 | 15.22 | 18.185 |
| OLANZAPINE | 1.0506 | 0.2278 | 4.61 | 28.8121 | 1.0681 | 0.0595 | 17.95 | 3.201 | 1.2 | 0.0507 | 23.67 | 32.0102 |
| Etoposide | 1.037 | 0.1142 | 9.08 | 15.5979 | 0.7273 | 0.0491 | 14.81 | 1.7329 | 1.2468 | 0.0929 | 13.42 | 17.3293 |
| Nefopam | 0.8859 | 0.1159 | 7.64 | 31.6802 | 1.1617 | 0.0329 | 35.31 | 3.5197 | 1.2368 | 0.0569 | 21.74 | 35.1967 |
| Suprofen | 1.4298 | 0.203 | 7.04 | 34.5789 | 1.0962 | 0.0233 | 47.05 | 3.8417 | 1.2203 | 0.0788 | 15.49 | 38.4172 |
| Iopanoic Acid | 1.252 | 0.0601 | 20.83 | 18.7617 | 0.8708 | 0.0323 | 26.96 | 2.0844 | 1.2318 | 0.0871 | 14.14 | 20.8443 |

Other Embodiments

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

The invention claimed is:

1. A composition consisting of active and inert ingredients, wherein the sole active ingredients are:
    (a) a fibrate selected from the group consisting of bezafibrate, binifibrate, ciprofibrate, clinofibrate, clofibrate, etofibrate, fenofibrate, and gemfibrozil; and
    (b) diflunisal, a diflunisal analog, cinnamic acid, or a cinnamic acid analog, wherein said diflunisal analog has the structure of formula (III):

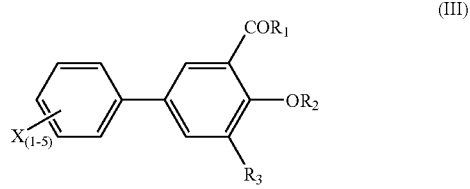

wherein each X is, independently, a halogen atom; $R_1$ is hydroxy, phenoxy, di($C_1$-$C_4$)alkylamino, di($C_1$-$C_4$)alkylamino, or ($C_1$-$C_4$)alkoxy; $R_2$ is hydrogen or ($C_1$-$C_4$)alkanoyl; and $R_3$ is hydrogen or methyl;
    wherein said cinammic acid analog has the structure of formula (II):

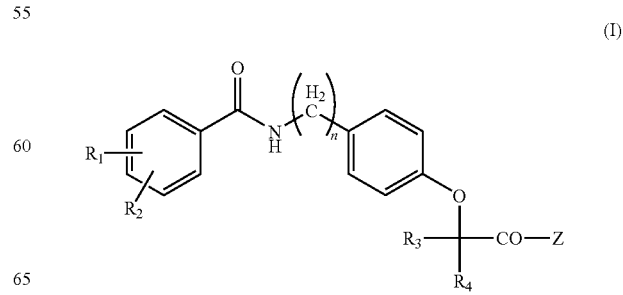

wherein $R_1$ and $R_2$ are each, independently, a hydrogen atom or a $C_{1-4}$ alkyl group; $R_3$ and $R_4$ each represent a hydrogen atom or may be combined together to form an additional chemical bond; n is zero or an integer from 1 to 3; each X is, independently, a hydroxyl group, a halogen atom, a straight or branched chain saturated or unsaturated $C_{1-4}$ alkyl group, a straight or branched chain saturated or unsaturated $C_{1-4}$ alkoxy group, a $C_{1-4}$ acyloxy group, or a $C_{3-6}$ cycloalkyl group; when n is 2 or 3 and two X's are commonly $C_{1-4}$ alkyl or $C_{1-4}$ alkoxy, both X's may be combined together to form a ring.

2. A composition consisting of active and inactive ingredients, wherein the sole active ingredients are bezafibrate and diflunisal.

3. A composition consisting of active and inactive ingredients, wherein the sole active ingredients are bezafibrate and cinnamic acid.

4. A composition consisting of active and inactive ingredients, wherein the sole active ingredients are:
    (a) bezafibrate or a bezafibrate analog having a structure of formula (I):

wherein $R_1$ and $R_2$ are each, independently, hydrogen, halogen, $C_{1-4}$ alkyl, or $C_{1-4}$ alkoxy; $R_3$ and $R_4$ are each, independently, hydrogen or $C_{1-4}$ alkyl; n is 1, 2, or 3; and Z is hydroxyl or $C_{1-4}$ alkyl; and (b) diflunisal, a diflunisal analog, cinnamic acid, or a cinnamic acid analog; wherein said diflunisal analog has the structure of formula (III):

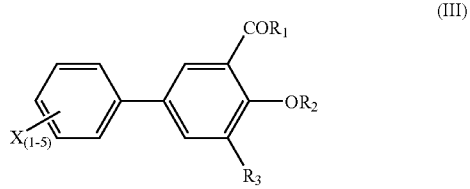

(III)

wherein each X is, independently, a halogen atom; $R_1$ is hydroxy, phenoxy, di($C_1$-$C_4$)alkylamino, di($C_1$-$C_4$)alkylamino, or ($C_1$-$C_4$)alkoxy; $R_2$ is hydrogen or ($C_1$-$C_4$)alkanoyl; and $R_3$ is hydrogen or methyl;

wherein said cinnamic acid analog has the structure of formula (II):

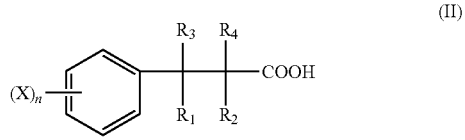

(II)

wherein $R_1$ and $R_2$ are each, independently, a hydrogen atom or a $C_{1-4}$ alkyl group; $R_3$ and $R_4$ each represent a hydrogen atom or may be combined together to form an additional chemical bond; n is zero or an integer from 1 to 3; each X is, independently, a hydroxyl group, a halogen atom, a straight or branched chain saturated or unsaturated $C_{1-4}$ alkyl group, a straight or branched chain saturated or unsaturated $C_{1-4}$ alkoxy group, a $C_{1-4}$ acyloxy group, or a $C_{3-6}$ cycloalkyl group; when n is 2 or 3 and two X's are commonly $C_{1-4}$ alkyl or $C_{1-4}$ alkoxy, both X's may be combined together to form a ring.

5. The composition of claim 4, wherein said bezafibrate analog is selected from the group consisting of alpha-[4-(2-methoxy-5-chlorobenzoylaminoethyl)-phenoxy]-isobutyric acid, alpha-[4-(4-methylbenzoylaminomethyl)-phenoxy]-isobutyric acid, alpha-[4-(2-methylbenzoylaminoethyl)-phenoxy]isobutyric acid, and alpha-[4-(4-chlorobenzoylaminoethyl)-phenoxy]-proprionic acid.

6. The composition of claim 4, wherein said bezafibrate or bezafibrate analog and said diflunisal, diflunisal analog, cinnamic acid, or cinnamic acid analog are present in amounts that, when administered to a patient, are sufficient to treat or reduce type II diabetes.

* * * * *

UNITED STATES PATENT AND TRADEMARK OFFICE
CERTIFICATE OF CORRECTION

PATENT NO. : 7,795,310 B2
APPLICATION NO. : 11/171566
DATED : September 14, 2010
INVENTOR(S) : Lee et al.

It is certified that error appears in the above-identified patent and that said Letters Patent is hereby corrected as shown below:

On Cover page, under OTHER PUBLICATIONS, in Yuan et al., replace "Science" with --*Science*--;

Under OTHER PUBLICATIONS, in Chen et al., replace "(1)",*Journal*" with --(1)", *Journal*--.

Column 2, Line 36, replace "clofibrinc" with --clofibric--;

Lines 64-65, replace "adeno sine" with --adenosine--.

Column 3, Line 52, replace "clofibrinc" with --clofibric--.

Column 6, Line 65, replace "lits" with --lists--.

Column 9, Line 63, replace "or more agent" with --or more agents--.

Column 12, Table 2, under mechanistic class, replace "andrenergic beta antagonist" with --adrenergic beta antagonist--;

Table 2, under therapeutic class, replace "dietary supplyment" with --dietary supplement--;

Table 2, under therapeutic class, replace "sedative/muscle relaxent" with --sedative/muscle relaxant--.

Column 13, Table 2, under chemical class, replace "mallic acid" with --malic acid--.

Column 17, under chemical class, replace "imdiazole" with --imidazole--;

Table 2, under chemical class, replace "thaizine" with --thiazine--.

Signed and Sealed this
Tenth Day of April, 2012

David J. Kappos
*Director of the United States Patent and Trademark Office*

CERTIFICATE OF CORRECTION (continued)

U.S. Pat. No. 7,795,310 B2

Column 18, Table 2, under mechanistic class, replace "phenolic antioxitant" with --phenolic antioxidant--;

Table 2, under mechanistic class, replace "vasodialator" with --vasodilator--;

Line 55, replace "overweight, is considered" with --overweight is considered--.

Column 21, Lines 45-46, replace "and blood collected" with --and blood was collected--;

Lines 50-54, replace "We have discovered compounds that the certain bezafibrate-containing combinations have in vitro and in vivo activities that suggest that these combinations may be useful for treating a patient that has been diagnosed with or is at risk of having a metabolic disorder." with --We have discovered that combinations of certain bezafibrate-containing compounds have in vitro and in vivo activities suggesting that these combinations may be useful for treating a patient who has been diagnosed with, or is at risk of having a metabolic disorder.--.

Column 24, Line 51, replace "each displaying" with --each displaying a--;

Line 55, replace "fibrates, binding to PPARα and glitazones, binding to" with --fibrates, binding to PPARα, and glitazones, binding to--.

Column 27, Line 31, replace "2,5 and 2,4-dimethylcinnamic acid" with --2,5- and 2,4-dimethylcinnamic acid--.

Column 28, Line 55, replace "in place diflunisal" with --in place of diflunisal--.

Column 29, Line 10, replace "HX0835. HYAL" with --HX0835, HYAL,--.

Column 32, Line 4, replace "Phenyloin" with --Phenytoin--.

Column 33, Line 33, replace "such as, intravenous" with --such as: intravenous--.

Column 37, Lines 28-29, replace "Harding et al. Nature 341: 758-7601" with --Harding et al. Nature 341: 758-760--;

Line 57, replace "532,248" with --5,532,248--.

Column 38, Line 38, replace "is an" with --is a--.

CERTIFICATE OF CORRECTION (continued)

U.S. Pat. No. 7,795,310 B2

Column 39, Line 8, replace "rapamycin, and has been" with --rapamycin and has been--;

Line 43, replace "listed on Table 1." with --listed in Table 1.--.

Column 44, Line 22, replace "can include, analyzing" with --can include analyzing--;

Line 29, replace "transcripts, and" with --transcripts and--;

Line 40, replace "include for example," with --include, for example,--.

Column 45, Line 1, replace "In: RNA" with --RNA--.

Column 46, Line 39, replace "adipocyte differentation" with --adipocyte differentiation--.

Column 47, Line 45, replace "blood collected" with --blood was collected--.

Column 48, Line 58, replace "adipocyte differentation" with --adipocyte differentiation--.

Column 50, Line 8, replace "subject, were" with --subject were--.

Column 53, Line 63-64, replace "di($C_1$-$C_4$)alkylamino, di($C_1$-$C_4$)alkylamino" with --di($C_1$-$C_4$) alkylamino--;

Column 53, Line 66, replace "cinammic acid" with --cinnamic acid--.